US007058616B1

(12) United States Patent
Larder et al.

(10) Patent No.: US 7,058,616 B1
(45) Date of Patent: Jun. 6, 2006

(54) METHOD AND SYSTEM FOR PREDICTING RESISTANCE OF A DISEASE TO A THERAPEUTIC AGENT USING A NEURAL NETWORK

(75) Inventors: Brendan Larder, Churchlane (GB); Dechao Wang, Cambridge (GB)

(73) Assignee: Virco Bvba, Beerse (BE)

( * ) Notice: Subject to any disclaimer, the term of this patent is extended or adjusted under 35 U.S.C. 154(b) by 0 days.

(21) Appl. No.: 09/589,167

(22) Filed: Jun. 8, 2000

(51) Int. Cl.
*G06N 3/02* (2006.01)
*C12Q 1/70* (2006.01)

(52) U.S. Cl. .............................. 706/15; 702/19; 435/5
(58) Field of Classification Search .................. 702/19, 702/20; 706/2, 13, 21; 435/5
See application file for complete search history.

(56) References Cited

U.S. PATENT DOCUMENTS

| 5,769,074 A | 6/1998 | Barnhill et al. ............. 128/630 |
| 5,845,049 A * | 12/1998 | Wu ............................. 706/16 |
| 5,860,917 A * | 1/1999 | Comanor et al. ........... 128/923 |
| 5,862,304 A | 1/1999 | Ravdin et al. ................ 395/22 |
| 5,898,792 A | 4/1999 | Öste et al. .................. 382/110 |
| 5,930,154 A | 7/1999 | Thalhammer-Reyero .... 364/578 |
| 5,953,727 A | 9/1999 | Maslyn et al. .............. 707/104 |

FOREIGN PATENT DOCUMENTS

WO    WO 97/27480    7/1997

OTHER PUBLICATIONS

Draghici et al. Correlation of HIV Protease Structure with Indinivir Resistance: a Data Mining and Neural Networks Approach. Proceedings of SPIE, vol. 4057, Apr. 2000, pp. 319-329 in: Data Mining and Knowledge Discovery: Theory, Tools and Technology.*
Abidi et al. Applying Knowledge Discovery to Predict Infectious Disease Epidemics : PRICAI '98 : Topics in Artificial Intelligence. Springer-Verlag, Berlin, Germany, 1998, pp. 170-181.*
Almeida et al.Application of Artificial Neural Networks to the Detection of *Mycobacterium* . . . Binary Computing in Microbiology (1995) vol. 7 No. 4-6, pp. 159-166.*
Ioannidis et al. (American Journal of Epidemiology (1998) vol. 147, No. 5, pp. 464-471).*
Harrigan et al. (AIDS (1999) vol. 13, No. 14, pp. 1863-1871).*
Allex et al., "Neural Network Input Representations that Produce Accurate Consensus Sequences from DNA Fragment Assemblies;" BioInformatics, vol. 15, No. 9, pp. 723-728 (Sep. 1999).
Alvager et al., "Neural Network Method to Analyze Data Compression in DNA and RNA Sequences," Journal of Chemical Information and Computer Sciences, vol. 37, pp. 335-337 (1997).
Bloor et al., "Lamivudine-Resistant HIV-1 Clinical Isolates Lacking the Met184Val Mutation Have Novel Polymorphisms in RT," Abstract 25 at 3rd International Workshop on HIV Drug Resistance & Treatment Strategies, Antiviral Therapy, vol. 4, Supp. 1, p. 19 (Jun. 23-26, 1999).
Bruisten et al., "Prospective Longitudinal Analysis of Viral Load and Surrogate Markers in Relation to Clinical Progression in HIV Type 1-Infected Persons" Aids Research and Human Retroviruses, vol. 13, No. 4, pp. 327-335 (1997).
Cai and Bork, "Homology-Based Gene Prediction Using Neural Nets," Analytical Biochemistry, vol. 265, pp. 269-274 (1998).
Chow and Cho, "Developmet of a Recurrent Sigma-Pi Neural Network Rainfall Forecasting System in Hong Kong," Neural Computing & Applications, vol. 5, pp. 66-75 (1997).
de Béthune et al., "Does Natural or Acquired Resistance to Reverse Transcriptase and Protease inhibitors, Observed in HIV-1 Groups M (Subtypes A-H) and O, Differ from Subtype B?," Abstract 49 at 3rd International Workshop on HIV Drug Resistance & Treatment Strategies, Antiviral Therapy, vol. 4, Supp. 1, p. 33 (Jun. 23-26, 1999).
Granjeon and Tarroux, "Detection of Compositional Constraints in Nucleic Acid Sequences Using Neural Networks," Computer Applications in the Biosciences, vol. 11, No. 1, pp. 29-37 (1995).
Hammer et al., "Relationship of Phenotypic and Genotypic Resistance Profiles to Virological Outcome in a Trial of Abacavir, Nelfinavir, Efavirenz and Adefovir Dipivoxil in Patients with Virological Failure Receiving Indinavir (ACTG 372)," Abstract 64 at 3rd International Workshop on HIV Drug Resistance & Treatment Strategies, Antiviral Therapy, vol. 4, Supp. 1, p. 45 (Jun. 23-26, 1999).
Hanke et al., "Self-Organizing Hierarchic Networks for Pattern Recognition in Protein Sequence," Protein Science, vol. 5, pp. 72-82 (1996).

(Continued)

*Primary Examiner*—Marjorie A. Moran
*Assistant Examiner*—Lori A. Clow
(74) *Attorney, Agent, or Firm*—Woodcock Washburn LLP

(57) ABSTRACT

A method and system for predicting the resistance of a disease to a therapeutic agent is provided. Further provided is a method and system for designing a therapeutic treatment agent for a patient afflicted with a disease. Specifically, the methods use a trained neural network to interpret genotypic information obtained from the disease. The trained neural network is trained using a database of known or determined genotypic mutations that are correlated with phenotypic therapeutic agent resistance. The present invention also provides methods and systems for predicting the probability of a patient developing a genetic disease. A trained neural network for making such predictions is also provided.

3 Claims, 9 Drawing Sheets

OTHER PUBLICATIONS

Harrigan et al., "Baseline HIV Drug Resistance Profile Predicts Response to Ritonavir—Saquinavir Protease Inhibitor Therapy in a Community Setting," AIDS, vol. 13, No. 14, pp. 1863-1871 (1999).

Harrigan et al., "Drug Resistance and Short Term Virological Response in Patients Prescribed Multidrug Rescue Therapy," Abstract 62 at 3rd International Workshop on HIV Drug Resistance & Treatment Strategies, Antiviral Therapy, vol. 4, Supp. 1, p. 43 (Jun. 23-26, 1999).

Hertogs et al., "Common, Rare and New Genotypic and/or Phenotypic HIV-1 Resistance Profiles Observed in Routine Clinical Practice: A Survey of Over 5000 Isolates," Abstract 108 at 3rd International Workshop on HIV Drug Resistance & Treatment Strategies, Antiviral Therapy, vol. 4, Supp. 1, p.75 (Jun. 23-26, 1999).

Hertogs et al., "A Rapid Method for Simultaneous Detection of Phenotypic Resistance to Inhibitors of Protease and Reverse Transcriptase in Recombinant Human Immunodeficiency Virus Type 1 Isolates form Patients Treated with Antiretroviral Drugs," Antimicrobial Agents and Chemotherapy, vol. 42, No. 2, pp. 269-276 (Feb. 1998).

Kashiwase et al., "A New Fluoroquinolone Derivative Exhibits Inhibitory Activity Against Human Immunodeficiency Virus Type 1 Replication," Chemotherapy, vol. 45, pp. 48-55 (1999).

Kemp et al., "Analysis of 5000 HIV-1 Clinical Samples Reveals Complex Non-Nucleoside RT Inhibitor Resistance Patterns," Abstract 26 at 3rd International Workshop on HIV Drug Resistance & Treatment Strategies, Antiviral Therapy, vol. 4, Supp. 1, p. 20 (Jun. 23-26, 1999).

Kemp et al., "A Novel Polymorphism at Codon 333 of Human Immunodeficiency Virus Type 1 Reverse Transcriptase Can Facilitate Dual Resistance to Zidovudine and L-2',3'-Dideoxy-3'-Thiacytidine," Journal of Virology, vol. 72, No. 6, pp. 5093-5098 (1998).

Kempf et al., "Analysis of Virological Response to ABT-378/Ritonavir Therapy in Protease Inhibitor-Experienced Patients with Respect to Baseline Viral Phenotype and Genotype," Abstract 8 at 3rd International Workshop on HIV Drug Resistance & Treatment Strategies, Antiviral Therapy, vol. 4, Supp. 1, p. 6 (Jun. 23-26, 1999).

Larder and Stammers, "Closing in on HIV Drug Resistance," Nature Structure Biology, vol. 6, No. 2, pp. 103-106 (Feb. 1999).

Larder et al., "A Family of Insertion Mutations Between Codons 67 and 70 of Human Immuno-deficiency Virus Type 1 Reverse Transcriptase Confer Multinucleoside Analog Resistance," Antimicrobial Agents and Chemotherapy, vol. 43, No. 8, pp. 1961-1967 (Aug. 1999).

Larder et al., "Potential Mechanism for Sustained Antiretroviral Efficacy of AZT-3TC Combination Therapy," Science, vol. 269, pp. 696-699 (1995).

Larder et al., "Predicting HIV-1 Phenotypic Resistance from Genotype Using a Large Phenotype-Genotype Relational Database," Abstract 59 at 3rd International Workshop on HIV Drug Resistance & Treatment Strategies, Antiviral Therapy, vol. 4, Supp. 1, p. 41 (Jun. 23-26, 1999).

Larder et al., "Tipranavir is Active Against a Large Selection of Highly Protease Inhibitor-Resistant HIV-1 Clinical Samples," Abstract 5 at 3rd International Workshop on HIV Drug Resistance & Treatment Strategies, Antiviral Therapy, vol. 4, Supp. 1, p. 5 (Jun. 23-26, 1999).

Lehne et al., "Challenging Drug Resistance in Cancer Therapy," Acta Oncologica, vol. 37, No. 5, pp. 431-439 (1998).

Lende and Csernai, "Classification of Genetic Sequences with Backpropagation," International Journal of Neural Systems, vol. 5, No. 3, pp. 159-163 (Sep. 1994).

Lennerstrand et al., "Mechanism of Zidovudine and Stavudine Resistance for HIV-1 RT with Amino Acid Insertions Between Codons 68 and 70," Abstract 32 at 3rd International Workshop on HIV Drug Resistance & Treatment Strategies, Antiviral Therapy, vol. 4, Supp. 1, p. 23 (Jun. 23-26, 1999).

Miller et al., "Phenotypic Susceptibility to Adefovir Dipivoxil in Clinical Samples with defined RT Genotypic Resistance Patterns," Abstract 40 at 3rd International Workshop on HIV Drug Resistance & Treatment Strategies, Antiviral Therapy, vol. 4, Supp. 1, p. 28 (Jun. 23-26, 1999).

Mills et al., "Article for Analog Vector Algebra Computation," BioSystems, vol. 52, pp. 175-180 (Oct. 1999).

Petropoulos et al., "A Novel Phenotypic Drug Susceptibility Assay for Human Immunodeficiency Virus Type 1," Antimicrobial Agents and Chemotherapy, vol. 44, No. 4, pp. 920-928 (Apr. 2000).

Rampone, "Recognition of Splice Junctions on DNA Sequences by BRAIN Learning Algorithm," BioInformatics, vol. 14, No. 8, pp. 676-684 (1998).

Sbirrazzuoli and Brunel, "Computational Neural Networks for Mapping Calorimetric Data: Application of Feed-Forward Neural Networks to Kinetic Parameters Determination and Signals Filtering," Neural Computing & Applications, vol. 5, pp. 20-32 (1997).

Schinazi et al., "Mutations in Retroviral Genes Associated with Drug Resistance," International Antiviral News, vol. 5, No. 8, pp. 129-142 (1997).

Tolstrup, "Pruning of a Large Network by Optimal Brain Damage and Surgeon: An Example from Biological Sequence Analysis," International Journal of Neural Systems, vol. 6, No. 1, pp. 31-42 (Mar. 1995).

Törönen et al., "Analysis of Gene Expression Data Using Self-Organizing Maps," FEBS Letters, vol. 451, pp. 142-146 (1999).

Uberbacher et al., "Discovering and Understanding Genes in Human DNA Sequence Using GRAIL," Methods in Enzymology, vol. 266, pp. 259-281 (1996).

Weber and Harrison, "Molecular Mechanics Analysis of Drug-Resistant Mutants of HIV Protease," Protein Engineering, vol. 12, No. 6, pp. 469-474 (Jun. 1999).

Wegner et al., "The Potential Role of Resistance Testing and Therapeutic Drug Monitoring in the Optimization of Antiretroviral Drug Therapy," Abstract 112 at 3rd International Workshop on HIV Drug Resistance & Treatment Strategies, Antiviral Therapy, vol. 4, Supp. 1, p. 77 (Jun. 23-26, 1999).

Wrede et al., "Peptide Design Aided by Neural Networks: Biological Activity of Artificial Signal Peptidase I Cleavage Sites," Biochemistry, vol. 37, pp. 3588-3593 (1998).

Wu, "Artifical Neural Networks for Molecular Sequence Analysis," Computers & Chemistry, vol. 21, No. 4, pp. 237-256 (1997).

Wu and Shivakumar, "Back-Propagation and Counter-Propagation Neural Networks for Phylogenetic Classification of Ribosomal RNA Sequences," Nucleic Acids Research, vol. 22, No. 20, pp. 4291-4299 (1994).

Ziermann et al., "A Mutation in Human Immunodeficiency Virus Type 1 Protease, N88S, That Causes In Vitro Hypersensitivity to Amprenavir," Journal of Virology, vol. 74, No. 9, pp. 4414-4419 (2000).

Zolopa et al., "A Comparison of Phenotypic, Genotypic and Clinical/Treatment History Predictors of Virological Response to Saquinavir/Ritonavir Salvage Therapy in a Clinic-based Cohort," Abstract 68 at 3rd International Workshop on HIV Drug Resistance & Treatment Strategies, Antiviral Therapy, vol. 4, Supp. 1, p. 47 (Jun. 23-26, 1999).

Zolopa et al., "HIV-1 Genotypic Resistance Patterns Predict Response to Saquinavir-Ritonavir Therapy in Patients in Whom Previous Protease Inhibitor Therapy Had Failed," Annals of Internal Medicine, vol. 131, No. 11, pp. 813-821 (Dec. 1999).

* cited by examiner (a)

(b)

METHOD AND SYSTEM FOR PREDICTING RESISTANCE OF A DISEASE TO A THERAPEUTIC AGENT USING A NEURAL NETWORK

The present invention relates to methods and systems for predicting the resistance of a disease to a therapeutic agent by application of genotype and phenotype resistance information in a neural network. The present invention further relates to methods and systems for designing a therapeutic treatment regimen for a patient based upon the genotype of the disease afflicting the patient. Under another aspect of the present invention, methods and systems for predicting the probability that a patient will develop a genetic disease are provided. More specifically, the present invention relates to the use of bioinformatic, molecular biology, and biochemistry tools in such methods and systems.

Since the issuance of the first report suggesting a correlation between the emergence of viral resistance and clinical progression, techniques to determine the resistance of a pathogen or malignant cell to a therapeutic agent have been increasingly incorporated into clinical studies of therapeutic regiments. Brendan Larder et al., HIV Resistance and Implications for Therapy (1998), herein incorporated by reference. With more drugs and therapeutic options becoming available, therapeutic agent resistance testing is expected to play an important role in the management and treatment of pathogen infection or cancer.

All of these methods employ two general approaches for measuring resistance to therapeutic agents, namely phenotypic testing and genotypic testing. Phenotypic testing directly measures the actual sensitivity of a patient's pathogen or malignant cell to particular therapeutic agents, while genotypic resistance testing examines the presence of specific genetic mutations or patterns of mutations in the pathogen or malignant cell that confer resistance to a certain therapeutic agent(s). Although phenotypic testing is believed to be a more comprehensive and accurate assessment of therapeutic agent resistance than genotypic testing, phenotypic testing can take longer and is generally more expensive than genotypic testing. Compared with phenotypic testing, genotypic testing has advantages, including the relative simplicity, low cost, and the speed with which the test can be performed. However, at present, it remains difficult to interpret the results of a genotypic test to provide meaningful conclusions about therapeutic agent resistance. See, e.g., Tim Horn and Spencer Cox, *A No-Nonsense Guide to HIV Drug Resistance Testing*, (Ed. Douglas Richman, M. D., University of California, San Diego.

A number of different approaches are presently available to aid in the interpretation of genotypic testing, including:

A. Interpretation by the Physician

A physician can interpret and make a judgement as to the optimum treatment based on knowledge of the primary resistance mutations associated with each therapeutic agent and the patient's recent treatment history. To assist physicians to make these judgements, various expert opinion-panels have been convened and have published guidelines. For example, the Resistance Collaborative Group has published such guidelines for HIV-1. See, e.g., Carpenter et al., *JAM* 283(3):381–390 (2000), herein incorporated by reference. Obviously, this type of method is highly subjective.

B. Rules-Based Algorithms

Rules-based algorithms are essentially a formalized version of the above-identified interpretation method with tables giving the mutations that are associated with resistance to each of the therapeutic agents. These can be simple printed tables or the information can be used to develop a rules-based computer algorithm. An example of such an interpretation system is the VircoGEN™ I system (available from Virco) and the techniques disclosed in WO 97/27480.

C. Statistical Analysis

Statistical analyses have been used to compare and relate phenotypes and genotypes. Harrigan et al., "Drug resistance and short term virological response in patients prescribed multidrug rescue therapy," 3rd International Workshop on HIV Drug Resistance & Treatment Strategies, San Diego, USA, 23–26 Jun. 1999; Hammer et al., "Relationship of phenotypic and genotypic resistance profiles to virological outcome in a trial of abacavir, nelfinavir, efavirenz and adefovir dipivoxil in patients with virological failure receiving indinavir (ACTG 372)," $3^{rd}$ International Workshop on HIV Drug Resistance & Treatment Strategies, San Diego, USA, 23–26 Jun. 1999; Zolopa et al., "A comparison of phenotypic, genotypic and clinical/treatment history predictors of virological response to saquinavir/ritonavir salvage therapy in a clinic-based cohort," $3^{rd}$ International Workshop on HIV Drug Resistance & Treatment Strategies, San Diego, USA, 23–26 Jun. 1999; Vingerhotes et al., "The accuracy and reproducibility of high throughput genotypic and phenotypic HIV-1 resistance testing under EN45001 and CLIA accreditation labels," $3^{rd}$ International Workshop on HIV Drug Resistance & Treatment Strategies, San Diego, USA, 23–26 Jun. 1999; Anton et al., "Comparative patterns of HIV-1 genotypic and phenotypic resistance profiles in gut and plasma," $3^{rd}$ International Workshop on HIV Drug Resistance & Treatment Strategies, San Diego, USA, 23–26 Jun. 1999; Hertogs et al., "A blinded comparative analysis of two genotyping service laboratories: full sequence analysis of HIV-1 protease and reverse transcriptase," $3^{rd}$ International Workshop on HIV Drug Resistance & Treatment Strategies, San Diego, USA, 23–26 Jun. 1999, all of which are herein incorporated by reference. These methods provid information about whether phenotypic data correlate to the corresponding genotypes. The faced difficulties, however, in relating quantitatively the genotype of any specific sample to its phenotype. Interpreting HIV-1 drug resistance mutation patterns has been improved by predicting the phenotype using a large phenotype-genotype database. To relate a "test" genotype to phenotypic resistance information, a series of genotypic patterns were related to specific drugs. These patterns are attached to all genotypic samples in the database thus enabling rapid searches to be performed. The phenotypes of samples in the database that match a particular genotype can then be retrieved and displayed as the proportion resistant or sensitive to each drug. Larder et al., Predicting HIV-1 phenotypic resistance from genotype using a large phenotype-genotype relational database, 3rd International Workshop on HIV Drug Resistance & Treatment Strategies, San Diego, USA, 23–26 Jun. 1999, herein incorporated by reference. This system makes it possible to obtain a rapid indication of the likely phenotype of a genotyped sample by matching substantial archived phenotypic data to a mutation pattern.

However, little is known about the functional form of the relationship between genotype and phenotype, therefore, making it difficult to utilize parametric modeling approaches. Furthermore, non-independent mutations in genotypic mutation patterns may be involved. This makes it difficult to apply conventional methods to perform function mapping between mutation patterns and the degree of drug resistance. Currently, however, there are improved relational databases that utilize pattern recognition and phenotypic matching, which have demonstrated a greater than 90% accuracy in predicting phenotypic resistance.

Pattern recognition and phenotype matching systems are implemented through software and use the mutations found in the patient sample to search for matches in a database of genotypes and phenotypes from thousands of samples. A search engine is used to scan a phenotype-genotype database. The phenotypes of samples in the database that match a particular genotype can then be retrieved and displayed as the proportion resistant or sensitive to each therapeutic agent. This type of system makes it possible to obtain a rapid indication of the likely phenotype of a genotyped sample by matching substantial archived phenotypic data to a mutation pattern. An example of such a software system is the VirtualPhenotype™ (available from Virco).

The present invention provides the next generation of software implemented pattern recognition and phenotype matching systems and employs a neural network to accurately predict the development of therapeutic agent resistance or sensitivity based upon genotypic and phenotypic information. Neural networks have been successfully used as pattern classifiers in many applications. See, e.g., Christopher M. Bishop, "Neural Networks for Pattern Recognition," Clarendon Press, Oxford, (1995); Sbirrazzuoli and Brunel, *Neural Comput & Applic.* 5:20–32 (1997); Chow and Cho, *Neural Comput & Applic.* 5:66–75 (1997), the disclosures of which are expressly incorporated herein by reference in their entireties. Until now, however, neural networks have not been used to predict therapeutic agent resistance or sensitivity.

To achieve these and other advantages, and in accordance with the principles of the present invention as embodied and broadly described herein, the present invention, in one aspect, provides a method and system for predicting therapeutic agent resistance using a neural network. According to one aspect, the present invention provides a method for predicting resistance of a pathogen to a therapeutic agent comprising: (a) providing a trained neural network; (b) providing a determined genetic sequence from the pathogen; and (c) predicting resistance of the pathogen to the therapeutic agent using the determined genetic sequence and the trained neural network.

The present invention further provides a method for predicting resistance of a disease to a therapeutic agent comprising: (a) providing a trained neural network; (b) providing a determined genetic sequence from the disease; and (c) predicting resistance of the disease to the therapeutic agent using the determined genetic sequence and the trained neural network.

Further provided in the present invention is a method for predicting resistance of a pathogen to a therapeutic agent comprising: (a) providing a neural network; (b) training the neural network on a training data set, wherein each member of the training data set corresponds to a genetic mutation that correlates to a change in therapeutic agent resistance; (c) providing a determined genetic sequence from the pathogen; and (d) predicting resistance of the pathogen to the therapeutic agent using the determined genetic sequence of the pathogen and the trained neural network.

The present invention also provides a trained neural network capable of predicting resistance of a disease to a therapeutic agent, wherein the trained neural network comprises: (a) a set of input nodes, wherein each member of the set of input nodes corresponds to a mutation in the genome of the disease; and (b) a set of output nodes, wherein each member of the set of output nodes corresponds to a therapeutic agent used to treat the disease.

In another embodiment, the present invention provides a method of designing a therapeutic agent treatment regimen for a patient afflicted with a disease comprising: (a) providing a determined genetic sequence from the disease; (b) inputting the determined genetic sequence into a trained neural network; (c) predicting resistance of the disease to a therapeutic agent using the determined genetic sequence and the trained neural network; and (d) using the predicted drug resistance to design a therapeutic drug treatment regimen to treat the patient afflicted with the disease.

Under a further embodiment, the present invention provides a method of predicting the probability of a patient developing a genetic disease comprising: (a) providing a trained neural network; (b) providing a determined genetic sequence from a patient sample; and (c) determining the probability of the patient of developing the genetic disease using the determined genetic sequence and the trained neural network.

It is to be understood that both the foregoing general description and the following detailed description are exemplary and explanatory only and are not restrictive of the invention, as claimed. Further features and/or variations may be provided in addition to those set forth herein. For example, the present invention may be directed to various combinations and subcombinations of the disclosed features and/or combinations and subcombinations of several further features disclosed below in the detailed description.

BRIEF DESCRIPTION OF THE DRAWINGS

The accompanying drawings, which are incorporated in and constitute a part of this specification, illustrate various embodiments and/or features of the invention and together with the description, serve to explain the principles of the invention. In the drawings.

DETAILED DESCRIPTION OF THE INVENTION

Figure 1:
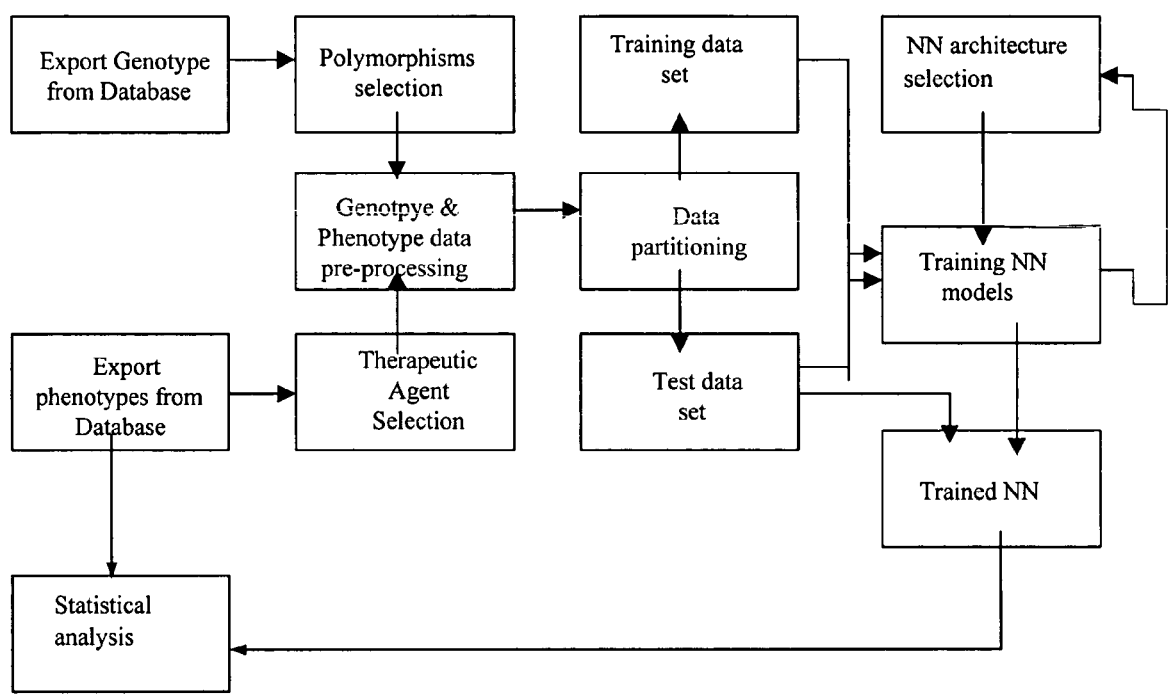
FIG. 1 depicts an exemplary framework for capturing the relationship between genotype and phenotypic resistance.
Figure 2:
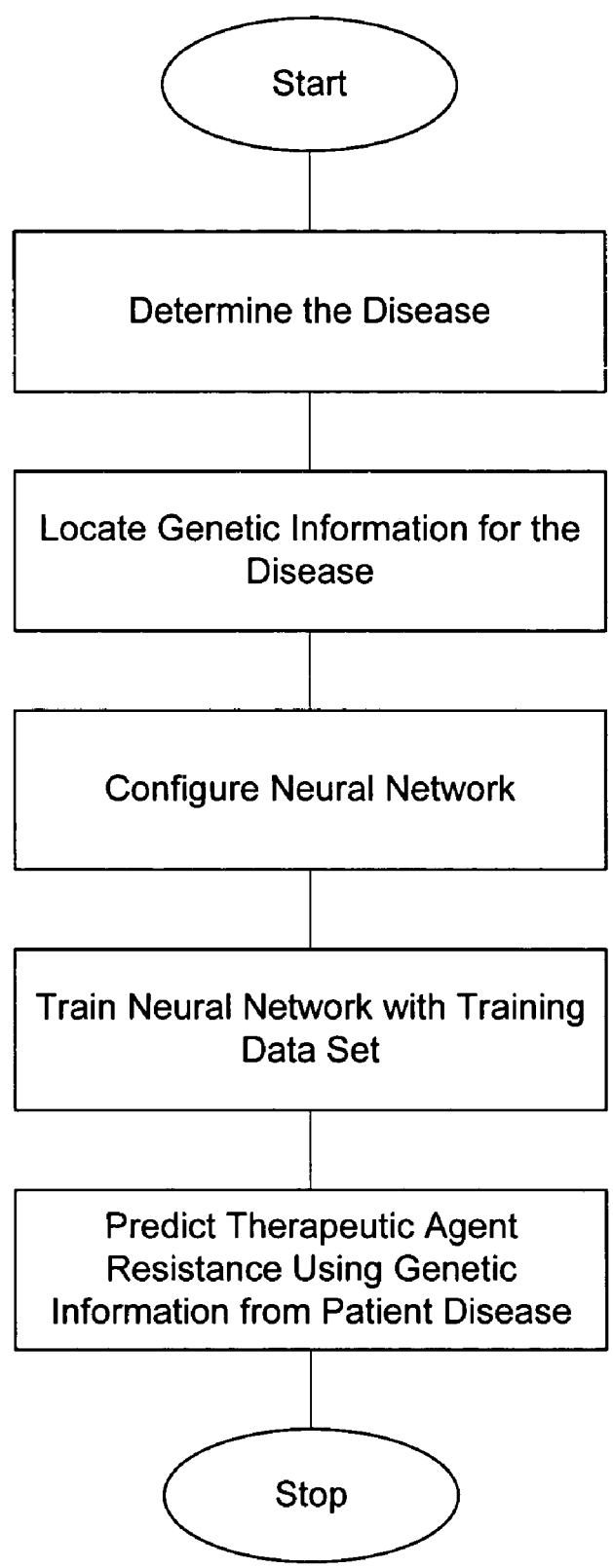
FIG. 2 depicts an exemplary flowchart for predicting phenotypic resistance based upon genotypic information using a neural network in accordance with the present invention.

Over time, many patients experience treatment failure or reduced efficacy. In many instances, this is due to mutations in the genome of the pathogen or malignant cell, which result in the development of resistance to a therapeutic agent. In other instances, selection by the therapeutic agent results in the accumulation or propagation of variants of the pathogen or malignant cell that had pre-existing resistance to the therapeutic agent. Accordingly, there is a need to monitor a patient's disease state and alter the therapeutic regimen when treatment failure or reduced efficacy occurs. As used herein, the term "disease" refers to a pathogen or malignant cell that causes a pathological condition in an organism from the pathogen's infection or malignant cell's replication.

The present invention describes a generic framework for predicting the resistance of a pathogen or malignant cell to a therapeutic agent. The generic framework of the present invention can be further used to identify mutation(s) or mutation patterns that confer resistance to a therapeutic agent. It is understood that the use of the term mutation also includes genetic polymorphisms. By employing bioinformatic tools to genotyping and phenotyping methodologies, the present invention accurately predicts resistance of patient's pathogen or malignant cell to a therapeutic agent based on genotypic mutations in the pathogen or malignant cell. First, the disease for which therapeutic resistance is to be predicted is selected. After the selection of the disease, a genotype-phenotype database of therapeutic resistance is located or created. Using this information, the neural network is configured and trained. With the trained network, it is possible to predict therapeutic agent resistance based upon genetic information from the patient's disease.

Under another embodiment, the generic framework of the present invention can be used to predict the development of a genetic disease in a patient. As used herein, the term "genetic disease" refers to any pathological condition that is directly or indirectly correlated to a genetic mutation. Under this embodiment, a phenotype-genotype database of genetic mutations correlated to with the development of a genetic disease is either located or generated. Using the data from this database, a neural network is trained. A sample from the patient's genetic information is genotyped. By inputting the patient's determined genetic information into the trained neural network, a prediction may be made as to the probability of the patient developing a given disease. Using this embodiment of the present invention, the probability of developing any genetic disease associated with a genetic mutation can be determined.

Accordingly, the present invention represents a paradigm shift in the ability of the clinician to monitor a patient's disease state and to accurately prescribe a therapeutic agent or combination of therapeutic agents based upon the pathogen's or malignant cell's existing or developed therapeutic agent resistance, and thereby most effectively treat the patient's disease state.

The present invention can predict the therapeutic agent resistance of any pathogen or malignant cell. A pathogen, as used herein, refers to any disease-producing microorganism, including bacteria, viruses, algae, fungi and protozoa. A malignant cell, as used herein, refers to a cell having the properties of anaplasia, invasion and metastasis.

The present invention has particular application to the prediction of therapeutic agent resistance of a disease-producing virus. Specifically, the present invention can predict the resistance of human immunodeficiency virus (HIV) type 1 and 2, herpes simplex virus (HSV) type 1 and 2, human papillomavirus virus, hepatitis B virus (HBV), hepatitis C virus (HCV), cytomegalovirus (CMV), rous sarcoma virus (RSV) and Epstein-Barr virus (EBV). The present invention has further particular application to the prediction of therapeutic agent resistance in such disease-producing bacteria as mycobacterium sp., salmonella sp., eschericia sp. and streptococcus sp.

Although some treatment regimens employ a single therapeutic agent, it is more typical today to employ a combination of therapeutic agents to treat any given disease-state. A therapeutic agent, as used herein, refers to any animal, vegetable, mineral, or pharmaceutical substance used to treat a pathogen or malignant cell. It is understood that the term "pharmaceutical substance" refers to pharmaceutical compounds, proteins, DNAs (including anti-sense DNA), RNAs. When a combination of therapeutic agents are employed and resistance develops, the clinician often does not know which therapeutic agent is no longer effective to treat the disease-state. Therapeutic agent resistance can be pre-existing or developed by prolonged exposure to one or more therapeutic agents.

The development of therapeutic agent resistance is especially troubling because, even today, a clinician only has a limited number of therapeutic agents available to treat any given pathogen or malignant cell. Thus, the clinician cannot simply replace all of the therapeutic agents presently being administered with a new set of therapeutic agents. For example, by replacing the current treatment regimen with a completely new treatment regimen, the clinician may discard an effective therapeutic agent. The clinician also cannot sequentially replace each therapeutic agent being administered in a combination therapy. Moreover, it is not uncommon for a pathogen or malignant cell, which displays resistance to a particular therapeutic agent to also display varying degrees of cross-resistance to other therapeutic agents.

Furthermore, not every mutation causes resistance. For example, a mutation can cause a pathogen or malignant cell to become more sensitive to a given therapeutic agent. Also a mutation can restore drug sensitivity to a pathogen or malignant cell that was previously resistant to that therapeutic agent.

By continual monitoring of the disease-state, the clinician will also be able to assess whether a more effective therapeutic agent can be prescribed to treat the patient. It is understood that the present invention can be equally used to detect the development of therapeutic agent sensitivity in a pathogen or malignant cell. By the use of the term therapeutic agent resistance, it is understood that this term includes both the increase and decrease in the sensitivity of the pathogen or malignant cell to a therapeutic agent.

Therefore, the present invention has particular application to monitoring the effectiveness of combination therapeutic agent treatment regimens. By monitoring the genotypic information of the pathogen or malignant cell, the clinician is able to more accurately assess the effectiveness of the present treatment regimen and prescribe the appropriate replacement therapeutic agent(s) as resistance or sensitivity develops.

Although the present invention is often stated in terms of the treatment of a human patient, it is understood that the present invention can be applied to measure the therapeutic agent resistance of a pathogen or malignant cell that causes a disease state in any animal.

A. Genotyping Methodologies

Genotyping methodologies detect specific genetic changes (mutations) in the genetic information of the sample. Under one embodiment of the present invention, the genotyping methodologies are used to detect specific genetic changes (mutations) in a pathogen or malignant cell genome that are known to be associated with therapeutic agent resistance. As used herein, the term "genome" is meant to refer to any DNA or RNA isolated from the pathogen or malignant cell. Thus, the term genome includes, for example, chromosomal DNA, extra-chromosomal DNA (including plasmid DNA, microsatellite DNA, and mitochondrial DNA), messenger RNA (MRNA), virally encoded DNA or RNA, and the like. These mutations can either make the pathogen or malignant cell more sensitive or more resistant to a therapeutic agent.

Under another embodiment of the present invention, the genotyping methodologies are used to detect specific genetic changes (mutations) in a patient's genome. Preferably, the genotyping methodologies of the present invention are used to detect mutations correlated with the development of a genetic disease. It is understood that not every mutation is directly correlated with a genetic disease. Sickle cell anemia is an example of a genetic mutation that is directly correlated with a genetic disease. Most mutations, however, are indirectly correlated with a genetic disease. These mutations generally increase the prevalence of a patient developing the genetic disease associated with the mutation, but the presence of the mutation, in and of itself, is not determinative of the development of the genetic disease. It is understood that the present invention has particular application to the prediction of the development of a genetic disease that is indirectly correlated to a mutation(s).

Genotyping is simpler to conduct than phenotyping and less expensive. One disadvantage is that the results are difficult to interpret. It is important to note that genotyping is not a measure of resistance on its own—resistance can be inferred from genotypic information but this requires sophisticated interpretation using such methods as described in the present invention.

It is understood that any method capable of detecting genetic changes can be used in the present invention. Moreover, these genetic changes can be detected in any DNA or RNA isolated from the sample. In addition, the genetic changes can be detected in cDNA prepared from the sample.

To perform genotypic analysis, a sample is collected. It is understood that the sample may be obtained from an individual of the species that is to be analyzed using any of a number of "invasive" or "non-invasive" sampling means. A sampling means is said to be "invasive" if it involves the collection of the sample from within the skin or organs of a patient. Examples of invasive methods include blood collection, semen collection, needle biopsy, pleural aspiration, etc. Examples of such methods are discussed by Kim et al., *J. Virol.*, 66:3879–3882 (1992); Biswas et al., *Annals NY Acad. Sci.* 590:582–583 (1990); Biswas et al., *Clin. Microbiol.* 29:2228–2233 (1991), all of which are herein incorporated by reference. In contrast, a "non-invasive" sampling means is one in which the sample is recovered from an internal or external surface of the patient. Examples of such "noninvasive" sampling means include swabbing, collection of tears, saliva, urine, fecal material, sweat or perspiration, etc.

Under one embodiment of the present invention, the DNA or RNA from the pathogen or malignant cell contained in the sample is isolated after the sample has been collected. Techniques for isolating DNA or RNA from a patient sample are known to persons of skill in the art and are fully described in Sambrook et al., *Molecular Cloning: A Laboratory Manual*, Vols. 1–3, $2^{nd}$ ed., Cold Spring Harbor Laboratory Press (1989), herein incorporated by reference. Such methods include, but are not limited to, mechanical disruption methods, chemical extraction methods, enzymatic digestion methods and freeze/thaw methods, or a combination of one or more of these methods.

The genotypic information is then determined from the isolated DNA or RNA. Alternatively, the genotypic information can be determined directly from the pathogen or malignant cell contained in the sample.

A determined genetic sequence as used herein refers to any DNA or RNA from the sample whose sequence has been determined, in whole or in part, preferably using one of the genotyping methodologies of the present invention. Two preferred methodologies suitable for determining genetic sequence are hybridization-based point mutation assays and DNA sequencing.

Hybridization-based point mutation assays search for individual known mutations. While these methods are highly specific, the point mutation assays are reported to only detect a fraction of these known mutations. For example, it has been reported that the LiPA test can only detect seven mutations in the RT gene of HIV-1 and none of the mutations related to protease resistance. See, e.g., Stuyver et al., *Antimicrob. Agents Chemotherap.* 41:284–291 (1997). Point mutation assays can, therefore, only provide a small select part of the resistance picture and then, as with all genotypic assays, the information collected has to be interpreted in terms of phenotypic resistance.

Common point mutation assays suitable for use in the present invention include, but are not limited to, primer-specific polymerase chain reaction (PCR) (see, e.g., Larder et al., *AIDS* 5: 137–144(1991); Richman et al., *J. Infect. Dis.* 164:1075–1081 (1991); Gingeras et al., *J. Infect. Dis.* 164: 1066–1074 (1991), all of which are herein incorporated by reference), differential hybridization (see, e.g., Eastman et al., *J. Acquir. Immune Defic. Syndr. Human Retrovirol.* 9: 264–273 (1995); Holodniy et al., *J. Virol.* 69:3510–3516 (1995); Eastman et al., *J. Clin. Micro.* 33:2777–2780 (1995), all of which are herein incorporated by reference), Line Probe Assay (LiPA™, Innogenetics) (Larder et al., *AIDS* 5: 137–144 (1991); Rossau et al., *Antimicrob Agents Chemother.* 41(10):2093–8 (1997); Stuyver et al., *Antimicrob. Agents Chemother.* 41(2):284–91 (1997), all of which are expressly incorporated herein by reference to their entireties); and gene chip sequencing (see, e.g., D'Aquila, *Clin. Diagnost. Virol.* 3: 299–316 (1995); Fodor et al., *Nature* 364:555–556 (1993); Fodor, *Nature* 227:393–395 (1997); U.S. Pat. Nos. 5,925,525, 5,861,242, and 5,834,758, all of which are expressly incorporated herein by reference).

DNA sequencing provides information on all the nucleotides in the region of the RNA or DNA sequenced. There are two main types of DNA sequencing methods, the so-called chain-termination method (see, e.g., Sanger and Coulson, *J. Mol. Bio.* 94:441–448 (1975), expressly incorporated herein by reference) and chemical sequencing (see, e.g., Maxam and Gilbert, *Methods Enzymol.* 65:499–560 (1980), expressly incorporated herein by reference). Both of these DNA sequencing methods are suitable for use in the present invention.

Preferably, only a segment or portion of the genetic information from the sample is used to detect a mutation. However, it is understood that the entire genome of a sample can be used to detect a mutation. As used herein, the phrase "mutation" refers to a specific genetic change in the nucleotide sequence of the sample in comparison to the genetic sequence at the same position or location in the wild-type sample. The genetic mutation is normally written as in reference to the wild type, i.e., K101N refers to replacement of a Lysine at codon 101 with an Asparagine. However, the mutations of the invention do not depend on the wild-type example listed in order to be within the practice of the invention. For example, the mutation 101N, refers to an Asparagine at the 101 codon regardless of the whether there was a Lysine at 101 prior to mutation.

Under one embodiment of the present invention, it is preferred to select a segment or portion of the genetic information that is known or believed to accumulate mutations that effect drug resistance. Under another embodiment, it is preferred to select a segment or portion of the genetic information from the patient sample that is known or believed to accumulate mutations correlated with the development of a disease. Generally, these segments are genes or fragments of genes encoding enzymes or proteins. Generally, these proteins are associated with the cell membrane. For example, in HIV, genes known to accumulate mutations that effect drug resistance include the polymerase gene, the protease gene and the reverse transcriptase gene.

The main challenge involved with genotyping is the interpretation of the results. Dependent on which method is used, some or all of the mutations that have occurred will be identified. However, the prediction of what the net effect of these mutations might be on the susceptibility of the pathogen or malignant cell population to the various therapeutic agents requires sophisticated interpretation. For example, extensive genetic analysis of resistant viral isolates generated through in vivo or in vitro selection has revealed that resistance is generally caused by mutations altering the nucleotide sequence at some specific site(s) of the genome. It is then up to the physician to combine this information with all the other information relating to the patient and decide what all this means in terms of selecting drugs for the treatment of their individual patient.

The mutational patterns that have been observed and reported for HIV-1 and that correlated with drug resistance are very diverse: some antiretroviral agents require only one single genetic change, while others require multiple mutations for resistance to appear. In HIV-1 there are currently approximately 100 mutations that are thought to be involved in the development of HIV-a therapeutic agent resistance. One such example is N88S, which causes in vitro hypersensitivity to amprenavir. See, e.g. Ziermann et al., *J. Virol.* 74(9):4414–9 (2000). A summary of mutations in the HIV genome correlated with drug resistance has been reported. Schinazi, R. F., Larder, B. A. & Meliors, J. W. 1997. *Int. Antiviral News.* 5, 129–142 (1997), herein incorporated by reference. Additionally, an electronic listing with mutations has also become available on the internet at sites such as hiv-web.lanl.gov or www.viraresistance.com.

The relationship between these point mutations, deletions and insertions and the actual susceptibility of HIV-1 to therapeutic agents is extremely complex and interactive. For example, the M184V mutation in HIV-1 confers resistance to 3TC reverses AZT resistance. See, e.g., Larder et al., *Science* 269:696–699 (1995), expressly incorporated herein by reference. The 333D/E mutation, however, reverses this effect and can lead to dual AZT/3TC resistance. See, e.g., Kemp et al., *J. Virol.* 72(6):5093–5098 (1998), expressly incorporated herein by reference.

When HIV-1 is genotyped, the preferred method for genotyping is the VircoGEN™ genotypic test (Virco). The VircoGEN™ is a genotyping assay that uses sequencing technology to identify all the known resistance mutations that have occurred in the protease—reverse transcriptase (PR-RT) genes of a patient's HIV-1 virus population. This is an indirect measure based on genetic indicators of therapeutic agent resistance.

The interpretation of genotypic data is both complex and critically important. As more therapeutic agents are developed and more mutations are correlated to the development of therapeutic agent resistance, this complexity will increase.

B. Phenotyping Methodologies

Phenotyping methodologies measure the ability of a pathogen or malignant cell to grow in the presence of different therapeutic agent(s) in the laboratory. This is usually expressed as the fold-change in the $IC_{50}$ or $IC_{90}$ values (the $IC_{50}$ or $IC_{90}$ value being the therapeutic agent concentration at which 50% or 90% respectively of the population is inhibited from replicating). A highly resistant pathogen or malignant cell might show a 50 or 100-fold increase in IC50, for example. Some mutations only increase the IC50 by as little as 2–3 fold.

Unlike genotyping, phenotyping is a direct measure of susceptibility, reflecting the effects and interactions of all the mutations, known or unknown, on the behavior of the pathogen or malignant cell population in the presence of therapeutic agent(s). While it is more difficult, time consuming and expensive to conduct, it is the "gold standard" of resistance testing.

Any method capable of measuring changes in the ability of a pathogen or malignant cell to grow in the presence of a therapeutic agent(s) can be used in the present invention. Such methods of phenotyping a pathogen or a malignant cell are known to persons of skill in the art.

For example and by way of illustration, methods for phenotyping pathogenic bacteria suitable for use in the present invention include, but are not limited to, measurement of inhibitory zone diameters (see, e.g., Guoming et al., *Sex. Transm. Dis.* 27(2):115–8 (2000), expressly incorporated herein by reference), colorimetric indicator methods (see, e.g., Lozano-Chiu et al., *Diagn. Microbiol. Infect. Dis.* 31(3):417–24 (1998), expressly incorporated herein by reference), and broth macrodilution method (see, e.g., Iwen et al., *J. Clin. Microbiol.* 34(7):1779–83 (1996), expressly incorporated herein by reference).

As an additional illustrative example, methods for phenotyping pathogenic viruses suitable for use in the present invention include, but are not limited to, plaque reduction assays, PBMC p24 growth inhibition assays (see, e.g., Japour et al., *Antimicrob. Agents Chemother.* 37:1095–1101 (1993); Kusumi et al., *J. Virol.* 66:875–885 (1992), both of which are expressly incorporated herein by reference), recombinant virus assays (see, e.g., Kellam & Larder, *Antimicrob. Agents Chemother.* 38:23–30 (1994); Hertogs et al., *5th International Workshop on HIV Drug Resistance*, Whistler, Canada. Abstr. 64 (1996); Hertogs et al., *Antimicrob. Agents Chemother.* 42:269–276 (1998); Hertogs et al., *International Workshop on HIV Drug Resistance Treatment Strategies and Eradication*, St. Petersburg, Fla., USA. Abstr. 43 (1997); and Pauwels et al., *2nd International Workshop on HIV Drug Resistance and Treatment Strategies*, Lake Maggiore, Italy. Abstr. 51(1998), all of which are expressly incorporated herein by reference); the use of GFP as a marker to assess the susceptibility of anti-viral inhibitors (Marschall et al., Institute of Clin. and Mol. Virol., University of Erlanger-Nuremberg, Schlobgarten, Germany); and cell culture assays (Hayden et al., *N. Eng. J. Med.* 321: 1696–702 (1989), herein incorporated by reference).

As yet another illustrative example, methods for phenotyping malignant cells suitable for use in the present invention include, but are not limited to, flow cytometric assays (see, e.g., Pallis et al., *Br. J. Haematol.* 104(2):307–12 (1999); Huet et al., *Cytometry* 34(6):248–56 (1998), both of which are expressly incorporated herein by reference), fluorescence microscopy (see, e.g., Nelson et al., *Cancer Chemother. Pharmacol.* 42(4):292–9 (1998), expressly incorporated herein by reference), calcein accumulation method (see, e.g., Homolya et al., *Br. J. Cancer.* 73(7): 849–55 (1996), expressly herein incorporated by reference), and ATP luminescence assay (see, e.g., Andreotti et al., *Cancer Res.* 55(22):5276–82 (1995), expressly incorporated herein by reference).

Under one preferred embodiment, the phenotype methodology employed in the present invention uses a detection enhancer. As used herein, a detection enhancer, or domain, may be a resonant, coloured, colourogenic, immunogenic, fluorescent, luminescent, or radioactive probe. The use of a detection enhancer increases the sensitivity of the phenotype methodology of the present invention and allows for increased automation and standardization of phenotyping. A detection enhancer may also be a proteinaceous molecule that can be detected, such as beta-galactosidase, luciferase, alkaline phosphatase, beta-lactamase, etc. A detection enhancer may also be any molecule that can be detected with conventional techniques used to tag proteinaceous molecules, including, but not limited to the application of epitope-specific antibodies. In one embodiment, a detection part encompasses a transcriptional regulator, such as the heterologous reporter system described in U.S. Pat. No. 5,776,675, herein incorporated by reference.

Preferably the detection enhancer is a fluorescent, a radioactive, a luminescent and/or a coloured molecule. Preferably the fluorescent molecule is fluorescent protein, hereby defined as any polypeptide capable of emitting a fluorescent signal detectable above the background fluorescence of an intact cell or membrane composition. Suitable fluorescent proteins include Red Fluorescent Protein (RFP) from species of IndoPacific sea anemone Discosoma, Green Fluorescent Protein (GFP) derived from Aequorea victoria, and functional parts, derivatives, analogues and/or functionally enhanced versions thereof. A non-limiting example of a functionally enhanced version of GFP is enhanced Green Fluorescent Protein (EGFP) as described in (Yang et al., *Nucleic Acids Res.* 24:4592–93 (1996)). RFP, GFP and enhanced versions of GFP (EYFP, EGFP, ECFP, and EBFP) are available from Clonetech. For the purpose of this invention, these polypeptides may be used interchangeably, and may be herein referred to collectively as GFP.

In one embodiment of the invention, the detection enhancer may comprise one or more components of a Fluorescence resonance energy transfer (FRET) system. Such aspects may also be used to design high throughput screening assays. FRET is a process in which an excited fluorophore (a resonance donor) transfers its excited state energy to a light absorbing molecule (a resonance acceptor). In the practice of the present invention, resonance donors and acceptors can be on the same or different molecules. In one embodiment, a reporter molecule comprising a membrane targeting domain, at least one high specificity protease recognition site, and a resonance donor detection domain can comprise a first molecule. The remaining component of the FRET system may then comprise a membrane targeting domain and a resonance acceptor domain. This second molecule may, but does not necessarily, contain a high specificity protease recognition site. Cleavage of the first molecule by the high specificity protease alters the common membrane association of the two molecules, thereby changing the resonance signal. Of course, other combinations of two-part FRET systems are readily apparent to the skilled practitioner. Resonant transfer systems which may be useful in generating and detecting a signal from the detection domain include those described in U.S. Pat. Nos. 5,047,321, 5,340,716, and 5,709,994, all of which are herein incorporated by reference.

Detection enhancers have been successfully used in the phenotyping of HIV-1. Pauwels et al., *J. Virol. Methods* 20:309–321 (1998); Paulous et al., *International Workshop on HIV Drug Resistance, Treatment Strategies and Eradication*, St. Petersburg, Fla., USA. Abstr. 46 (1997); and Deeks et al., *2nd International Workshop on HIV Drug Resistance and Treatment Strategies*, Lake Maggiore, Italy. Abstr. 53 (1998), all of which are herein incorporated by reference.

Under one preferred embodiment, a phenotype-genotype database is generated to correlate each of the known genotype mutations with changes in the phenotypic drug resistance of that pathogen or malignant cell. By generating such a database, the initial set-up time for the neural network is substantially reduced for the information from such databases are used to train and test the neural networks of the present invention. In certain circumstances, such phenotype-genotype databases have already been generated. It is understood, however, that the present invention can be practiced by establishing a phenotype-genotype database concurrently with the establishment and training of the neural network.

Under another preferred embodiment of the present invention, a phenotype-genotype database is developed that correlates known genotype mutations with the development of a genetic disease. Preferably, the genotype mutations are indirectly correlated with the development of a genetic disease. Genetic mutations correlated with the development of a genetic disease are generally known to person of skill in the art. For example, mutations in the p53 gene are correlated with the development of a number of genetic diseases (Gallagher et al., *Ann. Oncol.* 10:139–50 (1999); Lenz et al., *Clin. Cancer Res.* 4:1243–50 (1998); Trepel et al., *Leukemia* 11:1842–1849 (1997); Iwadate et al., *Int. J. Cancer* 69:236–40 (1996), all of which are herein incorporated by reference). Likewise, and by way of illustration, many diseases have been linked to genetic mutations, including thyroid diseases (Finke, *Exp. Clin. Endocrinol. Diabetes* 104 *Suppl.* 4:92–97 (1996), herein incorporated by reference); Alzheimer disease (Roses, *Neurogenetics* 1:3–11 (1997), herein incorporated by reference); endometriosis (Bischoff et al., *Hum. Reprod. Update* 6:37–44 (2000), herein incorporated by reference); hereditary bone tumors (McCormick et al., *Mol. Med. Today* 5:481–486 (1999), herein incorporated by reference); breast cancer (Chen et al., *J. Cell Physiol.* 181: 385–92 (1999); Beckmann et al., *J. Mol. Med* 75:429–39 (1997), both of which are herein incorporated by reference); and cervical carcinoma (Lazo, *Br. J. Cancer* 80:2008–18 (1999), herein incorporated by reference).

Because of the time and expense associated with phenotypic testing, these assays are generally not suitable for routine clinical screening. Likewise, because of the difficulties in translating genomic information into meaningful data, genotype screening by itself is not suitable for routine clinical screening. The present invention, however, bridges the gap between the more meaningful data obtained from phenotypic testing and the more readily obtainable data obtained from genotypic testing through the use of a neural network.

C. Neural Networks

Neural networks make neither the assumption of how outputs depend on inputs nor the assumption that inputs are independent. Instead, neural networks offer a very powerful and general framework for representing non-linear mapping from a set of input variables to another set of output variables. Moreover, neural networks represent non-linear functions of many variables in terms of superposition of non-linear functions of single variables. These non-linear functions of single variables are themselves adapted to the data as part of the training process so that the number of such functions only needs to grow as the complexity of the problem itself grows, and not simply as the dimensionality grows.

Figure 3:
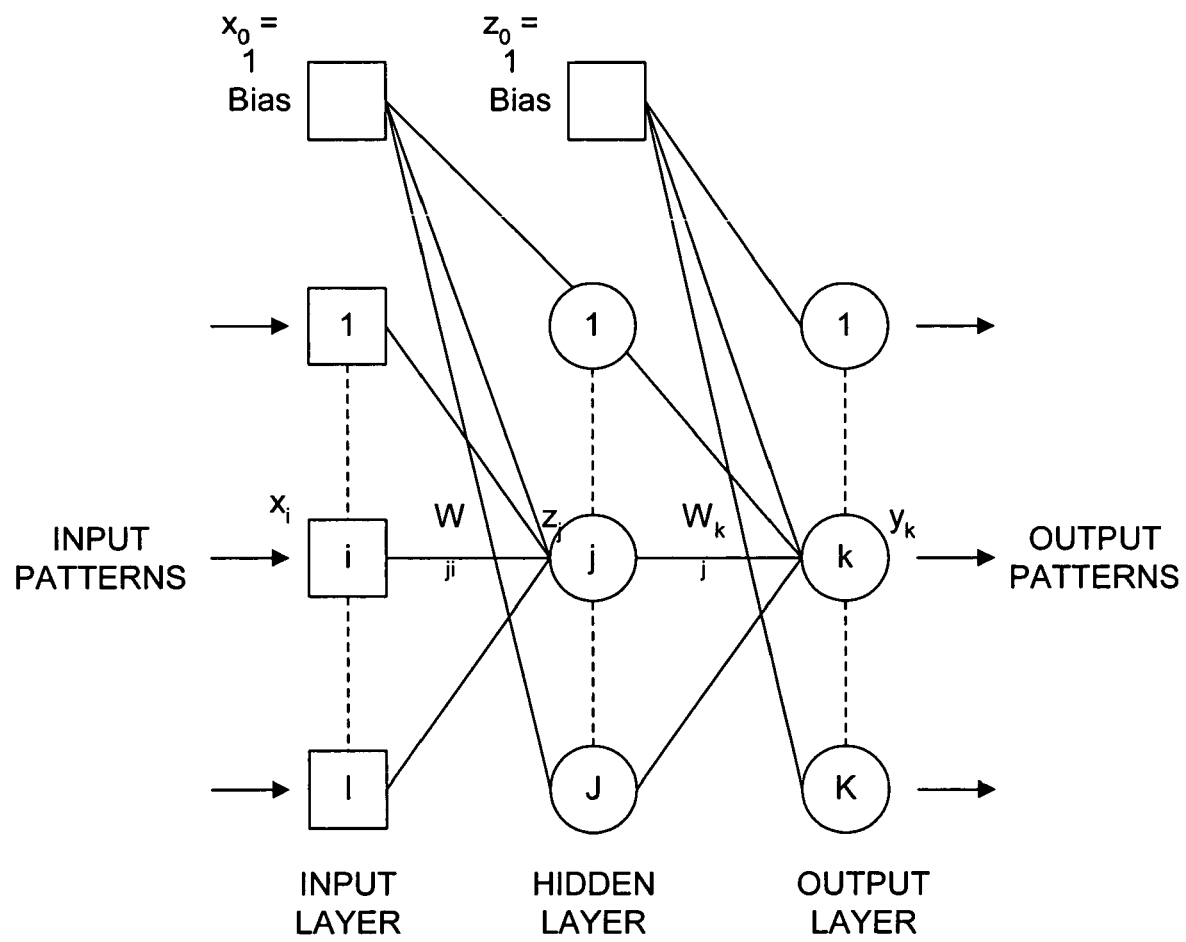
FIG. 3 depicts an exemplary framework for a three-layer neural network. This exemplary network has I inputs, J hidden units and K output units, and two bias units, both of which have an input signal of 1 (i.e., $x_o$ and $z_o$). This exemplary three-layer neural network also has two layers of adaptive weights ($w_{ji}$ and $W_{jk}$), which are the weight of the jth hidden unit associated with input signal $x_i$, and the weight of the kth output unit associated with the hidden signal $z_j$, respectively.

The neural network of the present invention is characterized by: (1) its pattern of connections between the neurons (called its architecture); and (2) its method of determining the weights on the connection (called its training or learning algorithm). FIG. 3 depicts an exemplary framework for a three-layer neural network.

1. Neural Network Architecture

According to an aspect of the present invention, a neural network is employed to model the relationship between genotype and phenotype for therapeutic agent resistance testing. According to another aspect of the present invention, a neural network is employed to identify mutation(s) or mutation patterns that confer resistance to a therapeutic agent.

Preferably, the neural network of the present invention employs a back-propagation learning algorithm implemented with supervised multi-layer perception (MLP) architecture. It is understood, however, that other forms of neural networks can be employed in the present invention. For example, adaline networks, adaptive resonance theory networks, bi-directional associative memory networks, back propagation networks, counter propagation networks, Hamming networks, Hopfield networks, Madaline networks, probabilistic neural networks, recirculation networks, spatio-temporal pattern recognition networks, and other types of neural networks can be used to achieve the objects of the present invention.

A neural network consists of a large number of simple processing elements called neurons (also referred to as nodes). The arrangement of neurons into layers and the connection patterns within and between layers is called the network architecture or architecture. Each neuron is connected to other neurons by means of directed communication links with an associated weight. Each neuron has an internal state, called its activation level, which is a function of the inputs it has received. Under one embodiment of the present invention, the activation level is bounded between 0 and 1. Under another embodiment, the activation level is bounded between −1 and 1.

Preferably, the neural network of the present invention is a feed-forward network where the signals flow from the input units to the output units in a forward direction. Preferably the feed-forward network of the present invention is a multi-level feed-forward network with one or more hidden layers. Under one preferred embodiment, the neural network of the present invention employs a single hidden layer.

Under one preferred embodiment, the feed-forward network of the present invention is fully connected where every node in each layer of the network is connected to every other node in the adjacent forward layer. However, it is understood that partially connected networks can also be employed in the present invention. Preferably, partially connected networks are employed where too much mutation or polymorphism input data is applied to the network. Alternatively, pruning techniques can be applied. It is understood that in a partially connected network, some of the communication links are missing from the network.

The action of the feed-forward network is determined by two things—the architecture and the value of the weights. The numbers of input and output nodes are determined by the number of mutations involved and the number of therapeutic agents being considered and so they are considered to be fixed. Initially, the value of the weights and biases are randomized. As training occurs, which is described in more detail below, the weights are adjusted to reduce the error function.

FIG. 3 depicts an exemplary framework for a three-layer neural network. The network has I inputs, J hidden units and K output units, and two bias units both of which have an input signal of 1 (i.e., $x_o$ and $z_o$). Preferably, the number of inputs, I, is equal to the number of mutations that are known to correlate to phenotypic therapeutic agent resistance for the disease being evaluated. However, under another embodiment, the number of input units, I, is equal to the number of mutations that are known to correlate to phenotypic therapeutic agent resistance for a gene existing in the disease being evaluated. For example, in HIV-1, the input, I, could equal all of the known mutations known to confer therapeutic agent resistance to HIV or it could equal all of the known mutations known to confer therapeutic agent resistance in the protease gene. Under a further sub-embodiment, only a sub-set of known mutations are inputted into the neural network of the present invention.

Each hidden layer, J, contains a plurality of hidden nodes. The number of hidden nodes, j, is considered to be a variable that can be adjusted to achieve good performance. In practice, the optimal number of hidden nodes is determined empirically. The means for determining the optimum number of nodes is well known to those of skill in the art and depends on the complexity of the genotype/phenotype information and disease being solved. Like the number of hidden layers, the number of hidden units also affect the complexity of the neural network. Preferably, the number of hidden units is determined by evaluation the performance of the neural network on the validation and test sets.

Preferably, the number of output units, K, is equal to the number of therapeutic agents with known mutations conferring resistance to the therapeutic agents. However, it is understood that the number of output units, K, can be a sub-set of therapeutic agents with known mutations conferring resistance. For example, the number of output units can be restricted to a particular class of therapeutic agents, such as protease inhibitors, etc.

The exemplary three-layer neural network of FIG. 3 has two layers of adaptive weights ($w_{ji}$ and $W_{jk}$), which are the weight of the jth hidden unit associated with input signal $x_i$, and the weight of the kth output unit associated with the hidden signal $z_j$, respectively. The values of these weights are optimized during the training step of the neural network, which is described below.

Under the embodiment of the present invention where mutation(s) and/or mutation pattern(s) are identified that confer resistance to a therapeutic agent, it is preferred that the number of inputs be equal to the number of mutations known to be correlated with conferring resistance to that therapeutic agent. Preferably, the number of outputs is equal to the number of therapeutic agents being studied by the present neural network for mutation identification.

Where the present invention is used to predict the probability of developing a disease, it is preferred that the number of inputs be equal the number of mutations known to be correlated with the development of the genetic disease(s). Under another embodiment, the number of inputs is equal to the number of mutations known to be correlated with the development of a given genetic disease. The number of outputs, preferably, is equal to the number of genetic disease(s) being evaluated by the neural network.

Under one embodiment of the present invention, the neural network employs a sigmoid curve as the activation function. The sigmoid curve can be binary (0, 1) or bipolar (−1, 1). Other activation functions that can be employed are linear, hyperbolic tangent, logistic, threshold and Gaussian functions.

2. Neural Network Training

Prior to inputting data into an input node, it must be pre-processed. Pre-processing refers to the process of converting molecular data into an input vector capable of being inputted into the neural network. Under one embodiment of the present invention, the mutation pattern x for a given sample is expressed by $x=(x_1, x_2, \ldots, x_n)$, where $x_i$ ($i=1, 2, \ldots, n$) has a value 0 or 1, with 1 representing the mutation occurring at position i, and 0 representing no mutation at position i, and n is the number of mutations in the test sample. The output data, likewise, needs to be pre-processed to convert the neural network data into meaningful data. Under one embodiment of the present invention, a fold resistance of less than or equal to 4 is considered to be "sensitive," greater than 4 and less than 10 is considered to be "intermediate," and if the value is greater than 10, it is considered to be "resistant."

Under one preferred embodiment, the neural network of the present invention employs a back-propagation (BP) learning rule. BP learning rules have been reviewed by, e.g., Chauvin and Rumelhart, Backpropagation: Theory, Architectures and Applications, Lawrence Erlbaum Assoc., Hillsdale, N.J. (1995), expressly incorporated herein by reference. BP algorithms provide a computationally efficient method for changing the weights in a feed-forward network with different activation functions.

BP training involves three stages: feed-forward of the input training pattern; calculation and back-propagation of the associated error; and adjustment of the weights. In the feed-forward phase, the weights remain unaltered throughout the network, and the function signals are computed on a neuron-by-neuron basis. In the back-propagation phase, error signals are computed recursively for each neuron starting at the output layer, and passed backward through the network, layer by layer to derive the error of hidden units. Weights are correspondingly adjusted to decrease the difference between the network's output and the target output. After training, the neural network only computes in feed-forward phase.

It is understood that the values of the free parameters (the weights and the biases) can be determined by minimizing the error function. One preferred error function that can be employed in the present invention is the root-mean-square error function, which is the square root of the sum-of-square errors calculated from all patterns across the training file. Other error functions are known to persons of skill in the art.

Under another preferred embodiment, the neural network of the present invention employs a counter-propagation (CP) program. See, e.g., Wu and Shivakumar, *Nucleic Acids Res.* 22:4291–4299 (1994), expressly incorporated herein by reference. A CP program approximates training input vector pairs by adaptively constructing a look-up table. In this manner, a large number of training data points can be compressed to a more manageable number of look-up table entries. The accuracy of the approximation is determined by the number of entries in the look-up table.

Under one embodiment of the present invention, BP and CP algorithms are used in combination. It has been reported that a network employing a combination of the two algorithms more accurately predicted phylogentic classifications than a network employing either algorithm alone. See, e.g., Wu and Shivakumar, *Nucleic Acids Res.* 22:4291–4299 (1994), expressly incorporated herein by reference.

In addition to BP training, other training algorithms can be employed in the present invention. For example, the pocket algorithm, delta rule, Hebb rule, Hopfield rule, Windrow-Hoff rule, adaline rule, and Kohonen rule can be used to train the neural network of the present invention.

In order to create a network having the best performance on new data, the simplest approach is to compare the error function of different networks using data that is independent of that used for training. By comparing the different networks, the effect of network parameter modifications can be easily measured.

Neural network parameters are determined by searching for the best performance on the test data set. With these parameters, a concordance rate of greater than 75% between genotype and phenotype can be achieved. Preferably, a concordance rate of greater than 85% is achieved. More preferably, a concordance rate of greater than 90% is achieved. It is understood, however, that concordance rates of greater than 95% can be achieved through the present invention.

Several internal parameters of the network of the present invention can be fine-tuned with the help of experimental results and experience. For example, the learning rate $\eta$ (the size step of the minimization process) can be optimized. The convergence speed of the neural network is directly related to the learning parameter. Too small of a leaning rate will make the training process slow, whereas too large of a learning rate may produce oscillations between poor solutions. In general, it is preferred to employ large steps when the search point is far from the minimum with decreasing step size as the search approaches its minimum. Suitable approaches for selecting the appropriate learning rate are provided by, e.g., Hassoun, Fundamentals of Artificial Neural Networks, MIT Press, Cambridge, Mass. (1995), expressly incorporated herein by reference. Preferably, the learning rate $\eta$ is set between 0.1 to 0.9. It is understood that the learning rate depends on the genotype-phenotype information being analyzed by the neural network.

Another internal parameter that can be optimized in the present invention is the momentum turn $\alpha$. Momentum allows the network to make reasonably large weight adjustments as long as the corrections are in the same general direction for several patterns, while using a smaller learning rate to prevent a large response to the error form any one training pattern. It also reduces the likelihood that the neural network will find weights that represent a local minimum. The momentum turn is normally chosen between 0 and 1. Preferably, the momentum $\alpha$ is set to 0.9.

Under one embodiment, a data set of genotypic and phenotypic data is collected. Preferably, the data set is collected from a phenotype-genotype database. Under one embodiment of the present invention, each member of the data set corresponds to a genetic mutation that is correlated to a phenotypic change in therapeutic agent resistance. Preferably the data set is divided into a training data set and a testing data set. It is not necessary to have a large training data set. If the samples in the training data set represent all possible cases with adequate statistical significance, the addition of new samples generally does not increase the amount to information in the training samples. Instead, it may decrease the useful amount of information to noise ratio in the samples. On the other hand, too small of a training data set will generally not cover all possible variations in the population. The resultant network often simply memorizes the data in the training data set and does not generalize properly.

During training, each member of the training data set is preferably presented to the neural network one datum at a time. For each member of the training data set, the network uses the preprocessed values to estimate a prediction, which is then compared with the actual resistance of the mutation. If the network's prediction is correct, the connection strengths and thresholds within the network are not changed and the next datum is presented. If the estimate of the prediction is not correct, the connection weights and thresholds in both the hidden layer and the output layer are adjusted to reduce the size of the error function. After the adjustments have been made, the next datum is presented. Training need not continue until the error actually meets its minimum. Training can be stopped once a threshold value for the error function (called tolerance) has been reached, or a fixed upper limit on the number of training iterations (called epochs) has been reached. Where error tolerance is used to determine the end-point of training, it is preferred that the error tolerance γ has a value between 0.1 and 0.0001. Under another embodiment, training is stopped once about 10,000 epochs have occurred.

Under one embodiment of the present invention, the training step is performed in an iterative fashion. In other words, a first training data set is selected from a phenotype-genotype database for training. This data set is then used to train the neural network. After the network has been trained, the prediction rate or concordance rate of the network is determined from a test data set. Samples which give an incorrect prediction are removed from the test data set and placed into a second training data set. The second training data set comprises the first data training set plus any samples that gave an incorrect prediction from the test data set. The second training data set is then used to re-train the neural network. If necessary, this process can be repeated until the desired performance level is achieved. By re-training the neural network in this fashion, it is possible to increase the performance of the neural network.

Occasionally, after the network has been trained and testing has begun, it is determined that the number of input units is excessive. When the number of input units is excessive, network training can be slowed and poor generalization can occur. The determination of what is an excessive number of inputs can be a subjective determination and depends on the specific network. However, if it is determined that the number of input units is excessive, it is preferred to reduce the number of input units. Therefore, under one embodiment, input trimming is used to reduce the dimensionality of the input data.

Under one embodiment of the present invention, a feature detector is employed that extracts salient features from the input data before presenting it to the neural network. For example, a data partition algorithm can be employed to sort non-spare data out, from which a testing set can be randomly selected. One such data partition algorithm is defined as follows:

$$d = \sum_{i=1}^{n} |x_i - z_i|$$

This algorithm calculates the distance (d) between any two mutation patterns (x and z), and makes it possible to sort spare data and noisy data out and avoid selecting them as testing members. The variable—n—is equal to the number of input units.

If the neural network continues to fail to correctly classify large portions of the samples in the training data set, even after repeated adjustments to the training algorithm parameters, the neural network complexity should be increased. On the other hand, if the neural network achieves a high rate of correctly classifying the training set, but fails to accurately classify a large number of samples in the testing data set, the network structure is probably too complex for the problem being solved. If this is the case, the number of nodes in the hidden layer(s) should be gradually reduced or if there are multiple hidden players, the number of hidden layers should be reduced.

Once the neural network has been trained, the network is ready and capable to predict the resistance of a disease to a therapeutic agent based upon the determined genetic sequence of the disease. To make this prediction, a patient sample containing a sample of the disease is isolated and the genetic information of the disease is determined. This determined genetic information is then pre-processed and loaded into the trained neural network. The trained neural network then computes the predicted resistance of the disease to a therapeutic agent.

Under another embodiment, the same trained neural network is used to identify additional mutation(s) and/or mutation pattern(s) that confer resistance to a therapeutic agent. In accordance with this embodiment, genetic mutations are identified in the determined genetic sequence. These genetic mutations are then inputted into the neural network and the neural network makes a prediction as to the phenotypic impact of these mutations on the resistance of the disease to a therapeutic agent. For example, the trained neural network can identify that a mutation previously associated with resistance to one therapeutic agent additionally confers resistance to another therapeutic agent.

Where the present invention is used to predict the development of a genetic disease in a patient, the neural network is trained in accordance with these methods using a training data set obtained from a phenotype-genotype database of known mutations that are correlated with the development of a genetic disease. Once the network has been trained, the genetic information from the patient sample is determined. Genetic mutations are identified from this sample and these genetic mutations are inputted into the trained neural network. The trained neural network is then able to make a prediction of the likelihood that these genetic mutations will lead to the development of a genetic disease in the patient.

The following examples are provided by way of illustration and are not intended to be limiting of the present invention.

EXAMPLE 1

Modeling the Relationship Between Genotype and Phenotype for HIV (Human Immunodeficiency Virus) Type 1 Drug Resistance

A. Genotyping Experiments

HIV-1 RNA was extracted from 200 µl of patient plasma using the QIAamp™ viral RNA extraction kit (Qiagen, Santa Clarita, Calif.), according to the manufacture's instructions. cDNA encompassing part of the pol gene was produced using Expand RT™. A 2.2 kb fragment encoding the protease and reverse transcriptase (RT) regions was then amplified by nested PCR. This genetic material was subsequently used in both phenotyping and genotyping experiments. See, e.g., Larder et al., *Antimicrob. Agents Chemother.* 43(8):1961–1967 (1999), expressly incorporated herein by reference. The PCR products obtained from patient plasma samples were genotyped by dideoxynucleotide-based sequence analysis, using Big Dye™ terminators (Applied Biosystems) and resolved on an ABI 377 DNA sequencer. See, e.g., Larder et al., *Antimicrob. Agents Chemother.* 43(8):1961–1967 (1999).

B. Phenotypic Experiments

Phenotypic susceptibility was determined using a MT-4 cell viral cytopathic effect protection assay. See, e.g., Kashiwase et al., *Chemotherapy* 45(1):48–55 (1999), expressly incorporated herein by reference; Larder et al., *Antimicrob. Agents Chemother.* 43(8):1961–1967 (1999). Fold resistance values are derived by dividing the mean 50% inhibitory concentration ($IC_{50}$) for a patient's recombinant virus by the mean $IC_{50}$ for wild-type control virus.

C. Data Pre-Processing

The genotypic and phenotypic data from a total of 172 samples was collected from a phenotype-genotype database. Each member of the data set corresponds to a genetic mutation that is correlated to a phenotypic change in therapeutic agent resistance. Among these samples, 20 were selected randomly as the members of the testing data set, the remaining 152 samples were selected as the members of the training data set. A total of 90 mutation positions were identified, 30 in the protease coding region, and 60 in the reverse transcriptase, as shown in Table 1 and Table 2.

TABLE 1

Mutations in the protease region

| | | | | | | | |
|---|---|---|---|---|---|---|---|
| 10 I | 10 R | 10 V | 20 M | 20 R | 24 I | 30 N | 32 I |
| 33 F | 36 I | 46 I | 46 L | 47 V | 48 V | 50 V | 54 A |
| 54 L | 54 V | 71 T | 71 V | 73 S | 77 I | 82 A | 82 F |
| 82 S | 82 T | 84 V | 88 D | 88 S | 90 M | | |

For a given sample, its mutation pattern x is expressed by $x=(x_1, X_2, \ldots x_{90})$ where $x_i(i=1,2,\ldots,90)$ has a value 0 or 1, with 1 representing the mutation occurring at position i, and 0 representing no mutation at position i.

The output variables y are represented by $y=(y_1, y_2, \ldots, y_{15})$, with $y_k$ (k=1, 2, ..., 15) denoting the fold resistance to drug k. They have values, which may differ by several orders of magnitude. By pre-processing, they were arranged for all of the outputs to be of order unity. For each variable, its maximum $y_{max}^i$ and minimum $y_{min}^i$ with respect to both training and testing data sets was calculated. A set of re-scaled variables is given by:

$$\tilde{y}_i^n = \frac{y_i^n - y_{min}^i}{y_{max}^i - y_{min}^i} * a + b$$

According to this formula, $y_i$ denotes fold resistance to drug i, $y_{min}^i$ denotes the minimum of $y_i$ in the whole samples, $y_{max}^i$ denotes the maximum of $y_i$ in the whole samples, n denotes the index of a specific sample, $y_i^n$ denotes fold resistance of the specific sample before pre-processing, $\tilde{y}_i^n$ denotes fold resistance of the specific sample after pre-processing, [b,a] is an interval to which fold resistance values are normalized, usually taken as [0,1].

D. Neural Network Implementation

In this example, a three-layer feed-forward neural network architecture was employed, with full interconnections from input units to hidden units and full interconnections from hidden units to output units. The input nodes were used to represent the genotypic mutations, and the output nodes the degrees of resistance to therapeutic agents, with their values denoting the fold resistance to each therapeutic agent. The hidden nodes were used to determine a suitable model order and achieve good performance. A back-propagation momentum algorithm (BP algorithm) was also used. The BP algorithm involves an iterative procedure for minimizing an error function, with adjustments to the weights being made in a sequence of steps. At each such step, back-propagation recursively computes the gradient or change in error with respect to each weight in the network and these values were used to modify the weights between network units.

Three layered neural network estimators, comprising 90 input units, 15 output units, and a single hidden layer with the number of units varying from 8 to 26, were trained and tested. The learning rate η was set to 0.1–0.9, the momentum a was set to 0.9, and the error tolerance γ, 0.1–0.0001. Training was terminated when the error tolerance was attained or when 10,000 epochs occurred, whichever happened sooner.

TABLE 2

Mutations in the reverse transcriptase region

| | | | | | | | |
|---|---|---|---|---|---|---|---|
| 41 L | 44 A | 44 D | 62 V | 65 R | 67 N | 69 D | 69 N |
| 69 S | 70 E | 70 R | 74 I | 74 V | 75 I | 75 M | 75 T |
| 77 L | 98 G | 98 S | 100 I | 101 E | 101 Q | 103 N | 103 Q |
| 103 R | 106 A | 106 I | 108 I | 115 F | 116 Y | 118 I | 151 M |
| 179 D | 179 E | 181 C | 181 I | 181 V | 184 I | 184 V | 188 C |
| 188 L | 189 I | 190 A | 190 Q | 190 S | 208 Y | 210 W | 211 K |
| 211 Q | 214 F | 215 C | 215 F | 215 Y | 219 E | 219 Q | 233 V |
| 236 L | 238 T | 333 D | 333 E | | | | |

Figure 4:
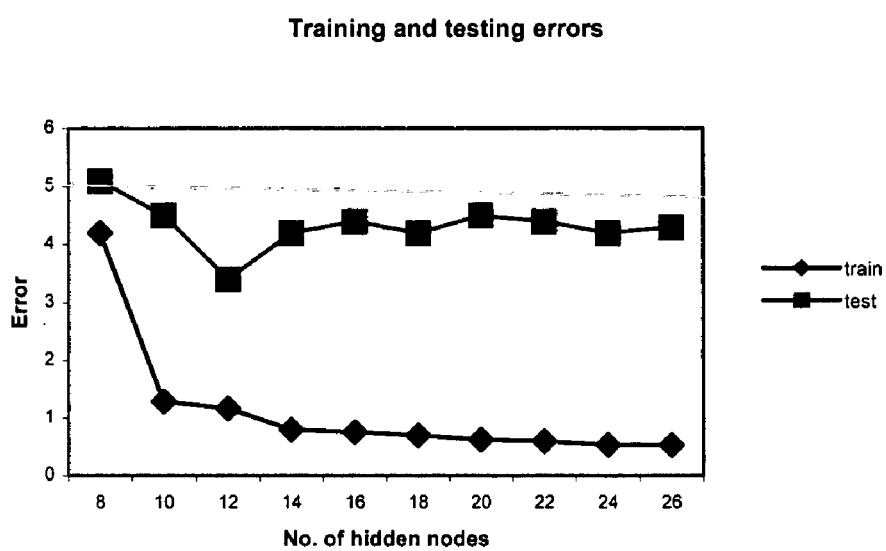
FIG. 4(a) is an exemplary comparison between the number of training and testing errors against the number of hidden nodes.
FIG. 4(b) is an exemplary comparison between the number of training and testing errors against the error tolerance index.
Figure 4:
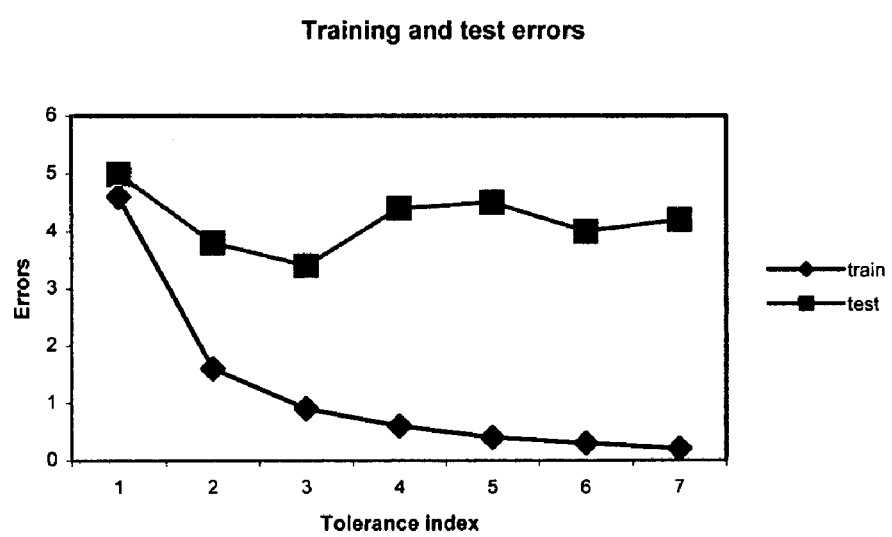

The training and testing results demonstrate that the neural network estimators with inadequate hidden units gave poor predictions for new data, and those with too many hidden units also exhibit poor generalization as shown in FIG. 4(a). The results also demonstrate that the performance did not get better when the error tolerance decreased, as shown in FIG. 4(b). In FIG. 4(b), the error tolerance index was 0.1 for Index 1, 0.05 for Index 2, 0.01 for Index 3, 0.005 for Index 4, 0.001 for Index 5, 0.0005 for Index 6 and 0.0001 for Index 7. This means good generalization was achieved by stopping training at an early stage. In these three-layered neural network estimators, the relevant network parameters were h (the number of hidden units), $\eta$, $\alpha$, and $\gamma$. A search in the parameter space showed that the optimal values of h, $\eta$, $\alpha$, and $\gamma$ are 12, 0.45, 0.9, and 0.01, respectively. With these neural network parameters, the performance of the neural network was evaluated based on 20 testing samples (each with 15 drugs), which were selected randomly from the same database as the training samples. Results from the test samples are summarized in Table 4.

The results also demonstrate that the 184V mutation has a strong effect on conferring 3TC resistance no matter what other mutations are involved.

TABLE 4

Simulating fold resistance conferred by mutation(s)

| | | Fold resistance | | | | |
|---|---|---|---|---|---|---|
| Index | Mutation(s) | AZT | 3TC | Nevi-rapine | Dela-virdine | DMP266 |
| P1 | 77I | 1.9 | 0.9 | 0.5 | 0.4 | 0.5 |
| P2 | 103N | 9.4 | 5.2 | 74.8 | 115.8 | 238.0 |
| P3 | 184V | 0.5 | 68.9 | 0.9 | 0.7 | 0.7 |
| P4 | 77I, 184V | 0.7 | 74.8 | 2.6 | 2.9 | 3.0 |
| P5 | 103N, 184V | 1.4 | 39.9 | 30.7 | 102.6 | 168.0 |
| P6 | 41L | 8.8 | 2.3 | 0.3 | 0.2 | 1.6 |
| P7 | 215Y | 13.7 | 1.3 | 0.2 | 0.1 | 0.3 |
| P8 | 41L, 184V, 215Y | 2.1 | 50.9 | 0.4 | 0.4 | 0.5 |
| P9 | 67N, 219Q | 22.7 | 2.8 | 0.2 | 0.1 | 0.6 |

TABLE 3

Drug resistance level and its prediction

| | 1 | 2 | 3 | 4 | 5 | 6 | 7 | 8 | 9 | 10 |
|---|---|---|---|---|---|---|---|---|---|---|
| AZT | S/S | I/R | R/R | S/R | S/I | R/S | S/S | S/R | I/S | I/I |
| 3TC | S/S | R/R | R/R | S/S | R/R | R/S | R/R | R/R | R/R | S/S |
| DDI | S/S | S/S | S/S | S/R | I/I | I/S | S/I | S/S | S/S | S/S |
| DDC | S/S | S/S | S/S | S/S | S/S | I/S | S/S | S/I | S/S | S/S |
| D4T | S/S | I/I | I/S | S/S | S/S | I/S | I/I | S/I | S/S | S/S |
| 1592 U89 | S/S | S/I | S/S | S/S | S/S | I/S | S/S | I/S | S/S | S/S |
| PMEA | S/S | S/S | S/S | S/S | S/S | S/S | R/R | S/S | S/S | S/S |
| Nevirapine | S/S | S/S | R/S | R/R | S/S | R/R | R/R | R/I | S/I | R/R |
| Delavirdine | S/S | S/S | R/R | R/R | S/S | R/I | R/R | R/R | S/S | R/R |
| DMP266 | S/S | S/S | R/R | R/R | S/S | R/I | S/S | R/R | S/S | R/I |
| Indinavir | S/S | S/S | I/R | I/R | R/R | R/S | S/S | I/R | S/S | S/R |
| Ritonavir | S/S | R/R | R/R | I/R | R/R | R/R | S/S | R/R | S/S | S/R |
| Nelfinavir | S/S | R/S | I/R | R/R | R/R | R/R | S/S | R/R | R/S | R/R |
| Saquinavir | S/S | S/S | I/R | I/I | I/I | I/S | S/S | S/R | S/S | S/I |
| VX-478 | S/S | S/I | S/S | S/I | S/I | S/S | S/S | S/S | S/S | S/S |

In Table 4, R stands for resistance, S, for sensitive, and I, for intermediate. A fold resistance of less than or equal to 4 is considered to be "sensitive," greater than 4 and less than 10 is considered to be "intermediate," and if the value is greater than 10, it is considered to be "resistant." The symbol "R/I" in Table 4 means that a sample is resistant to a drug from the phenotypic data and was predicted to be intermediate by the neural network model.

AZT (3'-azido-3'-deoxythymidine), ddI (2',3'-dideoxyinosine), PMEA (also known as adefovir, and 9-(2-phosphonylmethoxyethyl)adenine), VX-478 (also known as Amprenavir, Agenerase, and 141-W94) are approved potent inhibitors of a number of viruses.

Figure 5:
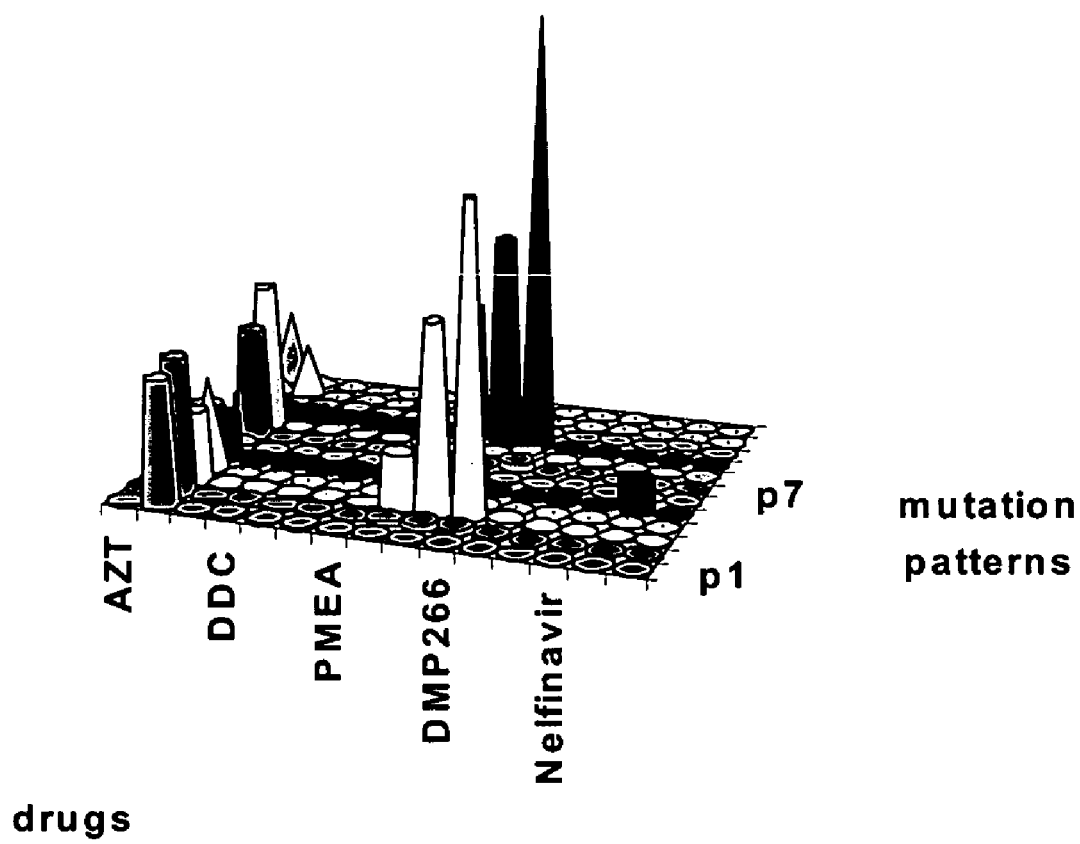
FIG. 5 is an exemplary plot of the magnitude of resistance for thirteen mutation patterns.

Simulation experiments were also conducted by combining different mutation patterns. A total of 13 mutation patterns, as shown in Table 4, were added to the testing data sets. The magnitudes of resistance that were simulated are shown in Table 4, and plotted in FIG. 5. It can be seen from the simulation results that the development of a 184V mutation can re-sensitize AZT-resistant virus if the 41L and 215Y mutations are already present in the RT of HIV-1. This confirms the biological observation that recombinant viruses containing the 184V mutation in the background of AZT resistance, such as 41L, 67N, 70R, 215Y and 219Q, cause a suppressive effect that result in reversion to AZT sensitivity.

TABLE 4-continued

Simulating fold resistance conferred by mutation(s)

| | | Fold resistance | | | | |
|---|---|---|---|---|---|---|
| Index | Mutation(s) | AZT | 3TC | Nevi-rapine | Dela-virdine | DMP266 |
| P10 | 67N, 184V, 219Q | 5.1 | 61.5 | 0.2 | 0.2 | 4.9 |
| P11 | 67N, 70R, 184V, 219Q | 4.1 | 81.0 | 0.2 | 0.1 | 3.3 |
| P12 | 67N, 70R, 215Y | 22.5 | 3.0 | 0.2 | 0.1 | 0.4 |
| P13 | 67N, 70R, 215Y, 219Q | 41.5 | 4.8 | 0.2 | 0.1 | 0.3 |

EXAMPLE 2

Predicting HIV-1 Protease Inhibitor (PI) Phenotypic Resistance from PI Genotype

In this example, the genotypic and phenotypic data from 1162 HIV-1 PI samples was collected from a genotype-phenotype database. A PI genotype refers to a genotype with a mutation or polymorphism in the protease coding region which is considered to conger resistance to a protease inhibitor. A total of 30 mutations were identified in the protease coding region, as shown in Table 1. For a given sample, its mutation pattern x was expressed by $x=(x_1, x_2, \ldots, x_{30})$, where $x_i (i=1,2,\ldots,30)$ has a value 0 or 1, with 1 representing the mutation occurring at position i, and 0 representing no mutation at position i.

TABLE 5

Drug resistance level and its prediction

|    | IDV | RTV | NFV | SQV | APV |
|----|-----|-----|-----|-----|-----|
| 1  | S/S | S/S | S/S | S/S | S/S |
| 2  | S/S | S/S | R/R | S/S | S/S |
| 3  | S/S | S/S | R/R | S/S | S/S |
| 4  | R/R | R/R | R/R | R/R | I/I |
| 5  | R/I | R/R | R/R | R/R | S/S |
| 6  | S/S | S/S | S/I | S/S | S/S |
| 7  | S/S | S/S | R/R | S/S | S/S |
| 8  | S/S | S/S | R/R | S/S | S/S |
| 9  | S/S | S/S | R/R | S/S | S/S |
| 10 | S/S | S/I | R/I | S/S | S/S |
| 11 | S/I | S/R | I/I | S/I | S/S |
| 12 | S/S | S/S | R/S | S/S | S/S |
| 13 | R/R | R/R | R/R | R/R | I/I |
| 14 | R/R | R/R | R/R | R/R | S/S |
| 15 | S/S | S/S | R/R | S/S | S/S |
| 16 | R/R | R/R | R/R | R/R | R/R |
| 17 | R/R | R/R | R/R | R/R | S/R |
| 18 | S/S | S/S | R/R | S/S | S/S |
| 19 | S/S | S/S | R/R | S/S | S/S |
| 20 | S/S | S/S | R/R | S/S | S/S |
| 21 | S/R | R/R | R/R | R/R | S/S |
| 22 | S/S | I/I | R/I | I/S | S/S |
| 23 | R/R | R/R | R/R | R/R | R/I |
| 24 | R/R | R/R | R/R | R/R | R/R |
| 25 | I/R | R/R | R/R | R/R | S/I |
| 26 | R/R | R/R | R/R | I/I | S/S |

Distance d between mutation pattern x and mutation pattern z was defined as follows:

$$d = \sum_{i=1}^{30} |x_i - z_i|$$

By calculating distance between any two mutation patterns, the distribution of the samples in a space was estimated. This made it possible to sort spare data and noisy data out and avoid selecting them as testing members.

Figure 6:
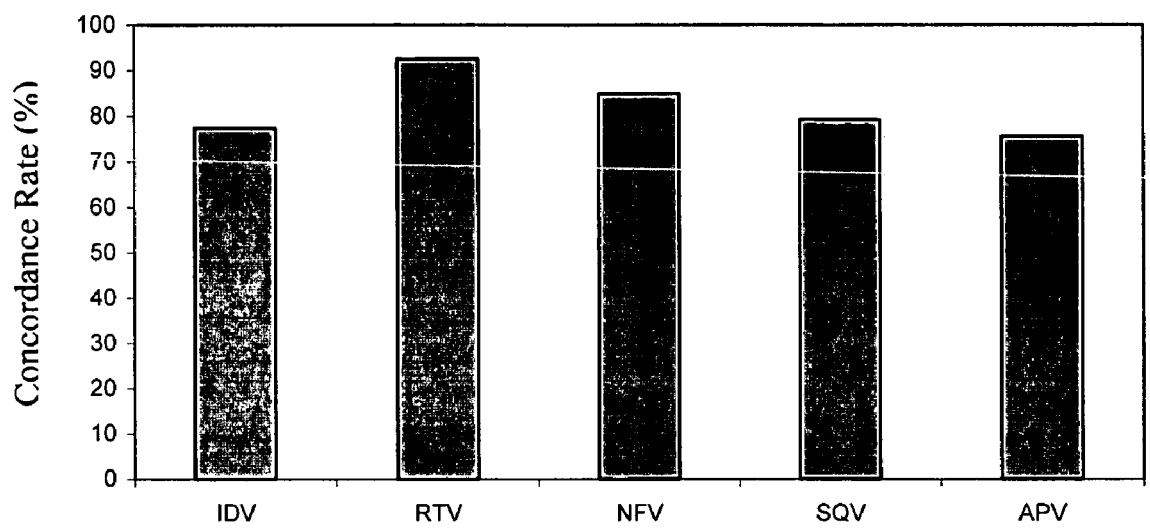
FIG. 6 is an illustrative graph of the concordance rate between PI genotypes and phenotypes from a neural network with noisy data involved in the training set.
Figure 7:
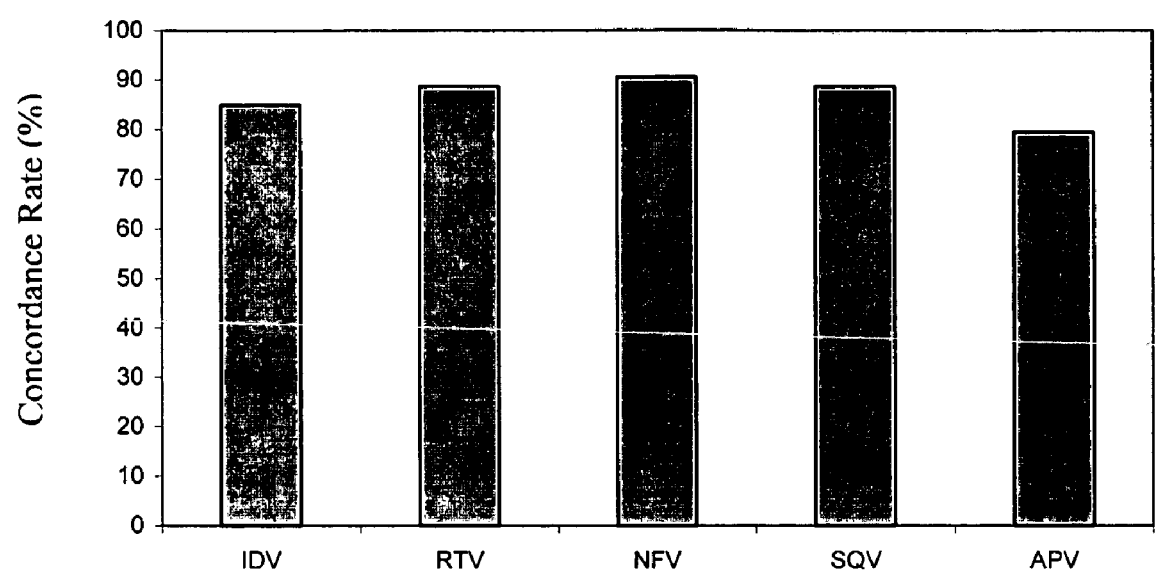
FIG. 7 is an illustrative graph of the concordance rate from a neural network without noisy data involved in the training set.

Three layered neural network estimators, comprising 30 input units, 5 output units (corresponding to 5 PI drugs) and a single hidden layer with the number of units varying were trained and tested. The performance of neural networks, which were trained with or without noisy data involved in the training set, is shown in FIG. 6 and FIG. 7. Concordance rates were from 76% for amprenavir (APV) to 93% for ritonavir (RTV) with an average of 82% for the network trained with noisy data. Concordance rates without noisy data were from 79% for amprenavir to 91% for nelfinavir (NFV) with an average of 86%. Thus, better performance was achieved when the noisy data was taken out from both training set and testing set.

TABLE 6

Drug resistance level and its prediction.

|    | IDV | RTV | NFV | SQV | APV |
|----|-----|-----|-----|-----|-----|
| 27 | R/R | R/R | R/R | S/R | S/S |
| 28 | R/R | R/R | R/R | S/S | S/S |

TABLE 6-continued

Drug resistance level and its prediction.

|    | IDV | RTV | NFV | SQV | APV |
|----|-----|-----|-----|-----|-----|
| 29 | R/R | R/R | R/R | R/R | S/S |
| 30 | R/R | R/R | R/R | R/R | I/I |
| 31 | R/R | R/R | R/R | R/R | R/I |
| 32 | R/R | R/R | R/R | R/R | R/I |
| 33 | I/R | R/R | R/R | I/I | S/S |
| 34 | S/S | S/I | R/R | S/S | S/S |
| 35 | R/R | R/R | R/R | I/R | I/S |
| 36 | R/R | R/R | R/R | R/R | I/I |
| 37 | I/I | S/R | R/R | S/S | S/S |
| 38 | R/R | R/R | R/R | R/R | I/S |
| 39 | R/R | R/R | R/R | R/R | I/I |
| 40 | R/R | R/R | R/R | R/R | S/I |
| 41 | I/S | I/I | R/R | I/S | S/S |
| 42 | S/S | I/S | I/I | R/S | S/S |
| 43 | I/S | R/R | I/S | S/S | S/S |
| 44 | I/R | R/R | R/R | R/R | I/I |
| 45 | R/R | R/R | R/R | R/R | S/S |
| 46 | R/R | R/R | R/R | R/R | I/I |
| 47 | R/R | R/R | R/R | R/R | I/S |
| 48 | R/R | R/R | R/R | R/R | S/S |
| 49 | R/R | R/R | R/R | R/R | I/I |
| 50 | S/S | R/I | S/S | S/S | S/S |
| 51 | R/R | R/R | R/R | R/R | S/I |
| 52 | S/S | S/S | R/R | S/S | S/S |
| 53 | R/R | R/R | R/R | R/R | I/S |

For the later neural network, the testing results are shown in Tables 5 and 6. With the same network, simulation experiments were conducted by combining different mutation patterns. The magnitudes of resistance that were simulated are shown in Table 7. The simulation results demonstrate that nelfinavir exhibits resistance with even a single mutation 30N or double mutations involved. This makes it different than other PI inhibitors. Resistance to indinavir (IDV), ritonavir and saquinavir (SQV) involve multiple mutations, usually greater than three mutations while resistance to amprenavir requires at least four mutations.

TABLE 7

Magnitude of resistance inferred from the model

| | Fold resistance | | | | |
|---|---|---|---|---|---|
| Mutation(s) | IND | RTV | NFV | SQV | APV |
| 10I | 1.1 | 3.2 | 1.4 | 0.2 | 0.1 |
| 30N | 1.1 | 2.0 | 13.9 | 0.7 | 0.5 |
| 36I | 1.9 | 3.0 | 5.4 | 0.6 | 0.2 |
| 46I | 1.2 | 3.4 | 2.7 | 0.2 | 0.1 |
| 71I | 1.4 | 2.0 | 3.6 | 0.4 | 0.2 |
| 73S | 2.4 | 5.0 | 6.8 | 0.7 | 0.1 |
| 82A | 0.4 | 1.0 | 0.5 | 0.1 | 0.1 |
| 84V | 3.8 | 8.3 | 8.4 | 4.0 | 1.0 |
| 88D | 1.1 | 3.8 | 1.3 | 0.3 | 0.1 |
| 90M | 1.5 | 6.2 | 4.3 | 1.3 | 0.1 |
| 30N 77I | 1.3 | 0.2 | 20.0 | 0.9 | 0.3 |
| 77I 88S | 2.3 | 1.8 | 13.0 | 2.1 | 0.8 |
| 36I 84V 90M | 22.8 | 39.0 | 37.0 | 30.8 | 9.2 |
| 54V 71V 73S | 17.9 | 51.1 | 44.8 | 5.0 | 0.4 |
| 82A 84V 90M | 10.6 | 34.8 | 10.3 | 12.6 | 4.7 |
| 48V 84V 90M | 12.4 | 21.9 | 20.8 | 20.6 | 6.0 |
| 10I 46I 84V 90M | 34.6 | 68.9 | 52.5 | 31.6 | 14.9 |
| 36I 46I 71V 84V | 33.2 | 74.0 | 47.0 | 13.5 | 11.1 |
| 46I 77I 84V 90M | 5.9 | 77.6 | 54.9 | 35.2 | 12.9 |
| 10I 46I 71V 84V 90M | 17.9 | 42.9 | 24.4 | 14.6 | 10.9 |
| 10I 46I 71V 77I 84V 90M | 45.0 | 77.3 | 58.4 | 34.0 | 11.9 |
| 10I 54V 71V 73S 77I 84V 90M | 34.3 | 108.5 | 69.0 | 49.1 | 10.7 |
| 10I 33F 71V 77I 84V 88D 90M | 9.3 | 43.8 | 12.0 | 16.5 | 9.1 |
| 10V 20M 36I 54V 71V 82A 84V 90M | 26.7 | 186.8 | 41.6 | 44.4 | 9.7 |

EXAMPLE 3

The Application of Neural Networks in Predicting Phenotypic Resistance from Genotypes for HIV-1 Protease Inhibitors In this example, a three-layer neural network model was constructed with 30 input nodes, corresponding to 30 mutations in the protease coding region and 5 output nodes, representing the fold resistance values for 5 protease inhibitors. A total of 1068 samples were selected from an HIV-1 phenotype-genotype database. Among these samples, 210 were selected as the testing data set, the remaining samples as the training data set. The performance of the neural network models was evaluated by calculating the prediction rate (concordance rate) in the test data set. An average prediction rate of 76% for 5 protease inhibitors was achieved for these data sets. In order to improve this prediction rate, samples that gave an incorrect prediction were removed from the test data set to the training data set and the neural network models was re-trained (with a training data set of 1015 samples and a test data set of 53 samples). With the re-trained neural network, an average prediction rate of 87% in the new test data set and an average concordance rate of 88% in the whole data set were obtained.

Next, an additional 60 protease gene polymorphisms were added to the input layer of the neural network model using the same training and test data sets. After training, the neural network gave an average prediction rate of 91% using the same new test data set and an average concordance rate of 92% in the whole data set. Linear regression analysis of the predicted versus actual fold resistance gave an $r^2$ value of 0.85 for the test data set. Analysis of this data set indicates that the improvement in prediction was due to the additional polymorphisms added to the model, such as 13V, 55R, 57K and 93L.

EXAMPLE 4

Modeling the Relationship Between Genotype and Phenotype for Stavudine (d4T) Using Neural Networks In this example, a total of 1182 samples with >4 fold d4T resistance were selected from a phenotype-genotype database for analysis. 105 samples were selected randomly as a test data set, the remainder was used as a training data set. By searching for the most frequent RT mutations in the database that are associated with stavudine resistance, 57 RT mutations were identified and used as the input variables for the neural network models. Following training, a prediction rate of 72% in the test set was achieved. In order to improve this prediction rate, samples which gave an incorrect prediction were removed from the test data set into the training data set and the neural network models were re-trained with a training data set of 1041 samples and a test data set of 41 samples. As a result, an average prediction rate of 85% in this new test set was achieved. Among these predictions, 84% gave the correct prediction of intermediate/intermediate (>4 fold change <10 fold change in stavudine sensitivity) and 89% gave the correct prediction of resistant/resistant (>10 fold resistance). 16% of the samples gave the incorrect intermediate/resistant prediction and 11% gave a resistant/intermediate prediction. Linear regression analysis of the predicted versus actual fold resistance gave a $r^2$ value of 0.67 for the test data set. These results demonstrate that the performance of the neural network model can be improved as the size of training data set is increased.

The neural network prepared according to this example was also able to identify mutation patterns that confer resistance to stavudine. Mutations previously known to confer stavudine resistance, such as 151 M and the "69 insertion" family were highlighted by this analysis. Additional mutational patterns that included AZT resistance mutations were also identified by the neural network as conferring resistance to stavudine. From these results, it appears that pathways other than multi-nucleoside resistance can confer stavudine resistance.

EXAMPLE 5

Another Application of Neural Networks in Predicting Phenotypic Resistance From Genotypes for HIV-1 Protease Inhibitors In this example, the interpretation of HIV-1 drug resistance mutation patterns has been improved by predicting the phenotype using a large phenotype-genotype database. To predict the phenotype from a genotype, the database is searched and phenotypes of samples matching the genotype are retrieved. The "virtual phenotype" is obtained by calculating the average increase in fold resistance for each drug in the matching group. To determine new mutation patterns, neural network techniques were adopted to determine the relationship between genotypes and phenotypes for the 5 currently licensed HIV-1 protease inhibitors. Three-layer neural network models were constructed with 30 input nodes, corresponding to 30 mutations in the protease coding region and 5 output nodes, representing the fold resistance values for 5 protease inhibitors. A total of 1068 samples were selected from a phenotype-genotype database for HIV-1. Among these samples, 210 were selected as the test data set, the remaining samples as the training data set. The performance of the neural network models was evaluated by calculating the prediction rate in the test data set. An average prediction rate of 76% to 5 protease inhibitors was achieved for these data sets. In order to improve this prediction rate, samples that gave an incorrect prediction were removed from the test data set to the training data set and the neural network models were re-trained (with a training data set of 1015 samples and a test data set of 53 samples). Now, an average prediction rate of 87% in the new test data set and an average concordance rate of 88% in the whole data set were obtained. Next, an additional 60 protease gene polymorphisms were added to the input layer of the neural network model using the same training and test data sets. After training, the neural network gave an average prediction rate of 92% using the same new test data set and an average concordance rate of 93% in the whole data set. Linear regression analysis of the predicted versus actual fold resistance gave an $r^2$ value of 0.85 for the test data set. Analysis of this data set indicated that the improvement (significant with p=0.036) in prediction was due to the additional polymorphisms added to the model, such as 13V, 55R, 57K and 93L.

In this Example, a generic framework of modeling the relationship between genotype and phenotype for HIV-1 drug resistance has been developed. Neural network models with 30 identified mutations and 90 mutations/polymorphisms were trained and tested. Improvement of prediction rate was observed and the corresponding additional polymorphisms that lead to the improvement were sorted out. Prediction comparisons were done in both testing data set and the whole data set studied. Analysis of this data set indicated that the improvement in prediction was due to the additional polymorphisms added to the model, such as 13V, 55R, 57K and 93L.

A. Neural Network Model

A generic framework was developed for modeling the relationship between genotypes and phenotypes of HIV-1 drug resistance as shown in FIG. 1. It consists of the following phases: determining NN architecture, collecting data, selecting mutations/polymorphisms and drugs, partitioning data, NN training and test, statistical analysis.

Neural Network Architecture:

The first step is to design a specific network architecture, including a specific number of "layers" each consisting of a certain number of "neurons." The size and structure of a neural network needs to match the nature of the HIV-1 drug resistance. However, the nature is obviously not known very well at this early stage. In order to determine a suitable network architecture, various networks, with a fixed number of hidden layer and different number of hidden units, were trained using a training data set. The performance of the neural networks was then evaluated and compared using a test set. The neural network architecture was finally determined by selecting the network having the best performance with respect to the test set.

Gathering Data for Neural Networks:

Neural networks learn from existing data. In order to investigate the relationship between genotypes and phenotypes of HIV-1 drug resistance using a NN, data needs to be gathered for training and test purposes. Both genotypes and phenotypes of samples were exported from a database into Excel files. Programs were designed to extract these genotypic data and phenotypic data for each individual sample. Phenotypic data consists of fold resistance to all drugs tested. Genotypic data contains all the polymorphisms in gag, reverse transcriptase, and protease coding regions.

Input and Output Variables:

The training set and test set include a number of cases, each containing values for a range of input and output variables. The choice of output variables is straightforward, depending on how many and which drugs are considered in the neural network models. The easiest way to select input variables is to consider all polymorphisms, even all sequence strings, as input variables. However, this may lead to a problem what is known as "the curse of dimensionality." As the number of input variables increases, the number of cases required increases non-linearly. In this Example, determining the input variables was guided initially by intuition. Expertise in HIV-1 drug resistance provided some idea of which variables are likely to be influential. For example, it is reasonable to select identified mutations and higher frequency polymorphisms as input variables.

Data Selection and Partitioning:

Selecting data and determining the number of cases required for neural network training presented difficulties. Neural network technologies rely on a key assumption that the training and test data must be representative of the underlying system. A neural network can only learn from cases that are present. If cases of sensitive phenotypes were not included in the training set, it is not expected that the neural network will make a correct decision when it encounters genotypes that associate to sensitive phenotypes. That is to say, the types of cases that are expected to predict must be covered in the training set. Since a neural network minimizes an overall error, the proportion of types of data in the set is also critical. A network trained on an unbalanced data set will bias its decision towards higher proportion of types. If the representation of the proportion of types is different in the real population, the network may not give a good decision. Generally speaking, the best approach for data selection is to ensure even representation of different cases, and to interpret the network's decisions accordingly. In this Example, 1162 cases were selected from the database, with each case having >10 fold resistance to at least one of the drugs. Data analysis showed that conflicting cases existed in the samples exported. These cases made it difficult to improve the performance of neural networks, and were then removed from the samples. Data analysis also demonstrated that data is not evenly distributed in the samples. Compared with the higher dimensional issue, the size of the training set seems still small. In this case, it is not suitable if the sparse cases are selected as test set. To address this issue, a data partition algorithm was designed to sort non-sparse data out, from which a test set was randomly selected. The remainder cases were taken as a training set.

Statistical Analysis:

In order to reasonably interpret results, statistical analyses were applied to the evaluation of the correlation between the predicted phenotypes and the actual phenotypes, and the testing of various statistical significances. The correlation coefficient that is far from zero provided four possible explanations about the relationship between the predicted and the actual phenotypes. The conclusion may be: that the predicted phenotypes help determine the values of the actual phenotypes; that another variable may also influence the actual phenotypes besides the predicted phenotypes; that the predicted phenotypes and the actual phenotypes do not correlate at all; or that a strong correlation was observed, as in this case. The p-value determines how often this could occur. The p-value of a result is the probability that the observed relationship in a sample occurred by pure chance, and that in the population from which the sample was drawn, no such relationship exists. The r squared provides information about how much percentage of variance is shared between the predicted and the actual phenotypes.

Predicting results on the test data set are summarized in tables 8 and 9, where R stands for resistance, S, for sensitive, and I, for intermediate. A fold resistance of less than or equal to 4 is considered to be 'sensitive', greater than 4 and less than 10 is considered to be 'intermediate', and if the value is greater than 10, it is considered to be 'resistant'. The symbol 'R/I' in tables 8 and 9 means that a sample is resistant to a drug from the phenotypic data and is predicted to be intermediate by the model.

TABLE 8

Predicting phenotypes against actual phenotypes

| | Indinavir | Ritonavir | Nelfinavir | Saquinavir | Amprenavir |
|---|---|---|---|---|---|
| 1 | S/S | S/S | S/S | S/S | S/S |
| 2 | S/S | S/S | R/R | S/S | S/S |
| 3 | S/I | S/S | R/R | S/S | S/S |
| 4 | R/R | R/R | R/R | R/R | I/I |
| 5 | R/I | R/R | R/I | R/I | S/S |
| 6 | S/S | S/S | S/S | S/S | S/S |
| 7 | S/S | S/S | R/R | S/S | S/S |
| 8 | S/S | S/S | R/R | S/S | S/S |
| 9 | S/S | S/S | R/R | S/S | S/S |
| 10 | S/S | S/S | R/S | S/S | S/S |
| 11 | S/I | S/I | I/I | S/S | S/S |
| 12 | S/S | S/S | R/S | S/S | S/S |
| 13 | R/R | R/R | R/R | R/R | I/I |
| 14 | R/R | R/R | R/R | R/R | S/S |
| 15 | S/S | S/S | R/R | S/S | S/S |
| 16 | R/R | R/R | R/R | R/R | R/R |

TABLE 8-continued

Predicting phenotypes against actual phenotypes

| | Indinavir | Ritonavir | Nelfinavir | Saquinavir | Amprenavir |
|---|---|---|---|---|---|
| 17 | R/R | R/R | R/R | R/R | S/R |
| 18 | S/S | S/S | R/R | S/S | S/S |
| 19 | S/S | S/S | R/I | S/S | S/S |
| 20 | S/S | S/S | R/R | S/S | S/S |
| 21 | S/R | R/R | R/R | R/R | S/S |
| 22 | S/I | I/I | R/I | I/I | S/S |
| 23 | R/R | R/R | R/R | R/R | R/R |
| 24 | R/R | R/R | R/R | R/R | R/R |
| 25 | I/R | R/R | R/R | R/R | S/S |
| 26 | R/R | R/R | R/R | I/S | S/S |

TABLE 9

Predicting phenotypes against actual phenotypes

| | Indinavir | Ritonavir | Nelfinavir | Saquinavir | Amprenavir |
|---|---|---|---|---|---|
| 27 | R/R | R/R | R/R | S/I | S/I |
| 28 | R/R | R/I | R/I | S/S | S/S |
| 29 | R/R | R/R | R/R | R/R | S/S |
| 30 | R/R | R/R | R/R | R/R | I/I |
| 31 | R/R | R/R | R/R | R/I | R/R |
| 32 | R/R | R/R | R/R | R/R | R/I |
| 33 | I/R | R/R | R/R | I/I | S/S |
| 34 | S/R | S/R | R/R | S/S | S/S |
| 35 | R/R | R/R | R/R | I/I | I/S |
| 36 | R/R | R/R | R/R | R/R | I/I |
| 37 | I/I | S/I | R/R | S/S | S/S |
| 38 | R/R | R/R | R/R | R/R | I/I |
| 39 | R/R | R/R | R/R | R/R | I/I |
| 40 | R/R | R/R | R/R | R/R | S/I |
| 41 | I/I | I/I | R/R | I/S | S/S |
| 42 | S/S | I/I | I/I | R/I | S/S |
| 43 | I/I | R/R | I/R | S/S | S/S |
| 44 | I/R | R/R | R/R | R/R | I/I |
| 45 | R/R | R/R | R/R | R/R | S/S |
| 46 | R/R | R/R | R/R | R/R | I/I |
| 47 | R/I | R/R | R/R | R/R | I/I |
| 48 | R/R | R/R | R/R | R/R | S/I |
| 49 | R/R | R/R | R/R | R/R | I/I |
| 50 | S/S | R/R | S/S | S/S | S/S |
| 51 | R/R | R/R | R/R | R/R | S/I |
| 52 | S/S | S/S | R/R | S/S | S/S |
| 53 | R/R | R/R | R/R | R/R | I/I |

An average prediction rate of 87% to 5 protease inhibitors was obtained in the new test data set. When an additional 60 protease gene polymorphisms, as shown in Table 10, were added to the input layer of the neural network model, the re-trained neural network model gave an average prediction rate of 92% in the same test data set. The predicting results using 90 mutations/polymorphisms are summarized in Tables 11 and 12.

TABLE 10

60 polymorphisms in the protease coding region

| 8D | 8Q | 10F | 13V | 20I | 20L | 20T | 20V |
|---|---|---|---|---|---|---|---|
| 22V | 23I | 24F | 32A | 33I | 33M | 33V | 33X |
| 36L | 36Q | 36R | 36T | 36V | 48T | 54S | 54T |
| 55R | 55T | 57K | 58E | 63A | 63C | 63H | 63I |
| 63N | 63P | 63Q | 63R | 63S | 63T | 63V | 71D |
| 71I | 71L | 73A | 73T | 73C | 82C | 82I | 82M |
| 84A | 84C | 84L | 85V | 88I | 88T | 89I | 89M |
| 89T | 89V | 93L | 93M | | | | |

By comparing Tables 8, 9 and Tables 11, 12, it was found that the improvement of phenotype prediction in the test data set happened in 23 of 53 samples, as listed in table 13, where the first letter denotes for the actual phenotype, the second, the predicted phenotype using 30 mutations, and the third, the predicted phenotype using 90 mutations/polymorphisms. The corresponding genotypic differences are summarized in Table 14.

Figure 8:
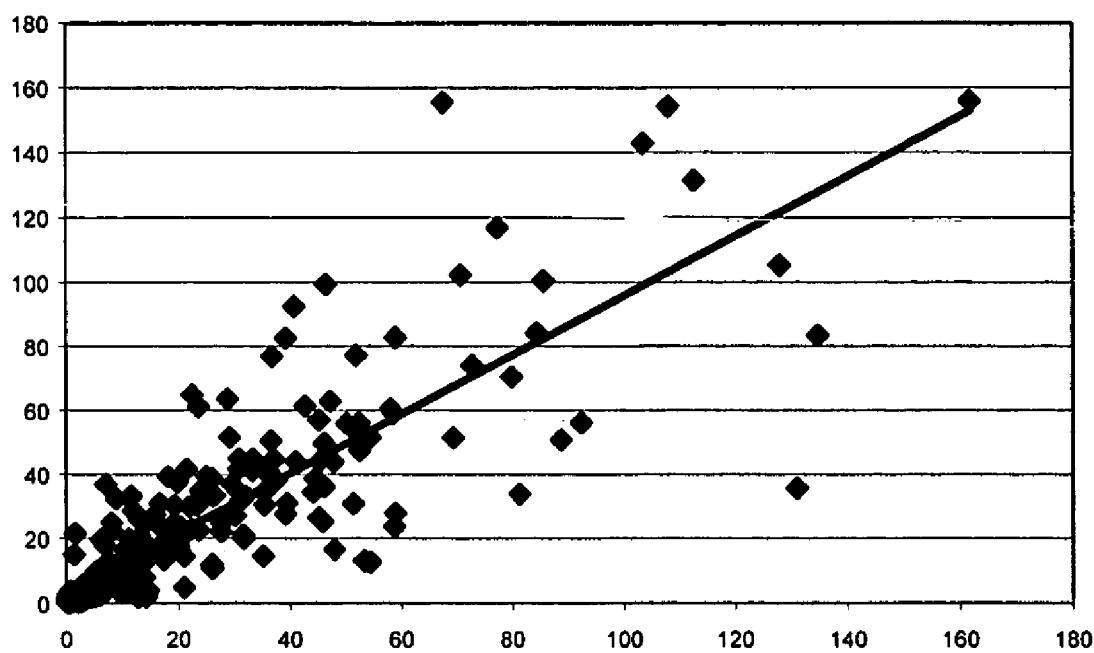
FIG. 8 provides a regression analysis between the predicted phenotypes and the actual phenotypes using 30 mutations.
Figure 9:
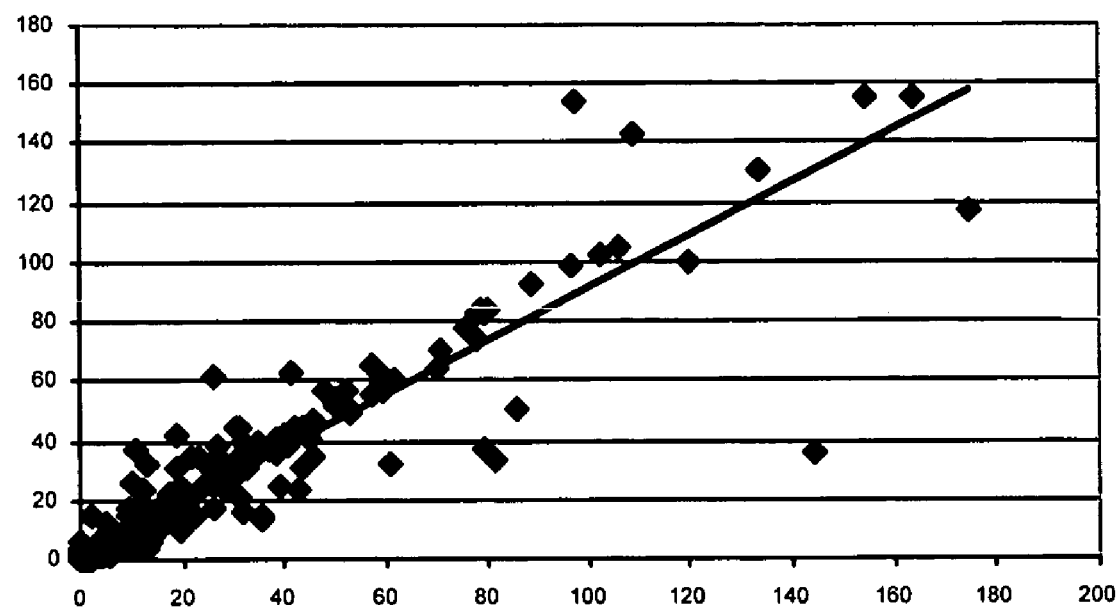
FIG. 9 provides a regression analysis between predicted phenotypes and the actual phenotypes using 90 mutations/polymorphisms.

Regression analyses of predicted phenotypes and the actual phenotypes are shown in FIGS. 8 and 9. In order to test whether the improvement is significant or not, the predicted distributions on the test data set in both cases are summarized in Tables 15 and 16 and the p-values are calculated as follows, S/S (0.187), I/I (0.382), and R/R (0.036). It can be seen that the improvement of predicted phenotypes from R to R is significant, although there is no evidence of significant improvement from S to S and I to I. Similar analyses were also done in the whole samples used in this work. The results indicated that the additional polymorphisms added to the model, such as 13V, 55R, 57K, and 93L, lead to the improvement in prediction.

TABLE 11

Predicting phenotypes using 90 mutations/polymorphisms against actual phenotypes

| | Indinavir | Ritonavir | Nelfinavir | Saquinavir | Amprenavir |
|---|---|---|---|---|---|
| 1 | S/S | S/S | S/S | S/S | S/S |
| 2 | S/S | S/S | R/R | S/S | S/S |
| 3 | S/S | S/S | R/I | S/S | S/S |
| 4 | R/R | R/R | R/R | R/R | I/I |
| 5 | R/I | R/R | R/R | R/R | S/S |
| 6 | S/S | S/S | S/S | S/S | S/S |
| 7 | S/S | S/S | R/R | S/S | S/S |
| 8 | S/S | S/S | R/R | S/S | S/S |
| 9 | S/S | S/S | R/R | S/S | S/S |
| 10 | S/S | S/S | R/S | S/S | S/S |
| 11 | S/S | S/S | I/I | S/S | S/S |
| 12 | S/S | S/S | R/R | S/S | S/S |
| 13 | R/R | R/R | R/R | R/R | I/I |
| 14 | R/R | R/R | R/R | R/R | S/S |
| 15 | S/S | S/S | R/R | S/S | S/S |
| 16 | R/R | R/R | R/R | R/R | R/R |
| 17 | R/R | R/R | R/R | R/R | S/I |
| 18 | S/S | S/S | R/R | S/S | S/S |
| 19 | S/S | S/S | R/R | S/S | S/S |
| 20 | S/S | S/S | R/R | S/S | S/S |
| 21 | S/R | R/I | R/R | R/R | S/S |
| 22 | S/I | I/R | R/R | I/I | S/S |
| 23 | R/R | R/R | R/R | R/R | R/R |
| 24 | R/R | R/R | R/R | R/R | R/R |
| 25 | I/I | R/R | R/R | R/R | S/S |
| 26 | R/R | R/R | R/R | I/S | S/S |

TABLE 12

Predicting phenotypes using 90 mutations/polymorphisms against actual phenotypes

| | Indinavir | Ritonavir | Nelfinavir | Saquinavir | Amprenavir |
|---|---|---|---|---|---|
| 27 | R/R | R/R | R/R | S/R | S/I |
| 28 | R/R | R/R | R/R | S/S | S/S |
| 29 | R/R | R/R | R/R | R/R | S/S |
| 30 | R/R | R/R | R/P | R/R | I/I |
| 31 | R/R | R/R | R/R | R/R | R/R |
| 32 | R/R | R/R | R/R | R/R | R/R |
| 33 | I/I | R/R | R/R | I/I | S/S |
| 34 | S/S | S/I | R/I | S/S | S/S |
| 35 | R/R | R/R | R/R | I/I | I/S |
| 36 | R/R | R/R | R/R | R/R | I/S |
| 37 | I/I | S/I | R/R | S/S | S/S |
| 38 | R/R | R/R | R/R | R/R | I/I |
| 39 | R/R | R/R | R/R | R/R | I/I |
| 40 | R/R | R/R | R/R | R/R | S/S |

TABLE 12-continued

Predicting phenotypes using 90 mutations/polymorphisms against actual phenotypes

|    | Indinavir | Ritonavir | Nelfinavir | Saquinavir | Amprenavir |
|----|-----------|-----------|------------|------------|------------|
| 41 | I/S       | I/R       | R/R        | I/S        | S/S        |
| 42 | S/I       | I/I       | I/I        | R/R        | S/S        |
| 43 | I/I       | R/R       | I/I        | S/S        | S/S        |
| 44 | I/I       | R/R       | R/R        | R/R        | I/I        |
| 45 | R/R       | R/R       | R/R        | R/R        | S/S        |
| 46 | R/R       | R/R       | R/R        | R/R        | I/I        |
| 47 | R/R       | R/R       | R/R        | R/R        | I/R        |
| 48 | R/R       | R/R       | R/R        | R/R        | S/S        |
| 49 | R/R       | R/R       | R/R        | R/R        | I/I        |
| 50 | S/S       | R/R       | S/S        | S/S        | S/S        |
| 51 | R/R       | R/R       | R/R        | R/R        | S/I        |
| 52 | S/S       | S/S       | R/R        | S/S        | S/S        |
| 53 | R/R       | R/R       | R/R        | R/R        | I/I        |

TABLE 13

Improvement of predicting phenotypes from using 30 mutations to using 90 polymorphisms

|    | Indinavir | Ritonavir | Nelfinavir | Saquinavir | Amprenavir |
|----|-----------|-----------|------------|------------|------------|
| 1  |           |           | R/I/R      | R/I/R      |            |
| 2  | S/I/S     | S/I/S     |            |            |            |
| 3  |           |           | R/S/R      |            |            |
| 4  |           |           |            |            | S/R/I      |
| 5  |           |           | R/I/R      |            |            |
| 6  |           | R/R/I     |            |            |            |
| 7  |           | I/I/R     | R/I/R      |            |            |
| 8  | I/R/I     |           |            |            |            |
| 9  |           |           |            | S/I/R      |            |
| 10 |           | R/I/R     |            |            |            |
| 11 |           |           | R/I/R      |            |            |
| 12 |           |           |            |            | R/I/R      |
| 13 | I/R/I     |           |            |            |            |
| 14 | S/R/S     | S/R/I     |            |            |            |
| 15 |           |           |            |            | I/I/S      |
| 16 |           |           |            |            | S/I/S      |
| 17 | I/I/S     | I/I/R     |            |            |            |
| 18 | S/S/I     |           | R/I/R      |            |            |
| 19 |           |           |            | I/R/I      |            |
| 20 | S/I/S     |           | R/R/I      |            |            |
| 21 | I/R/I     |           |            |            |            |
| 22 | R/I/R     |           |            |            | I/I/R      |
| 23 |           |           |            |            | S/I/S      |

TABLE 14

Genotypic differences, which lead to improvement of predicting phenotypes

|    | Identified mutations          | Additional polymorphisms |
|----|-------------------------------|--------------------------|
| 1  | 10I,71V,73S,84V,90M           | 63P,85V,93L              |
| 2  | 10I,46I,48V,77I,82A,90M       | 10E,58E,63T              |
| 3  | 10I                           | 36V,93L                  |
| 4  | 10I,46I,71V,77I,84V,90M       | 63P,93L                  |
| 5  | 10V,30N                       | 13V,63P                  |
| 6  | 10I,48V,54V,82A               | 13V                      |
| 7  | 71V,73S,90M                   | 20I,63P                  |
| 8  | 10I,54V,71V,73S,84V,90M       | 33M,63P                  |
| 9  | 10I,46L,54V,71V,82A,90M       | 63P,93L                  |
| 10 | 46I,71V,73S,90M               | 20I,63P,93L              |
| 11 | 10I,46L,54V,71V,77I,82A,90M   | 55R,58E,63P,93L          |
| 12 | 10I,36I,46I,84V,90M           | 20I,63P,73C,85V          |
| 13 | 10I,36I,71T,90M               | 63P,73T                  |
| 14 | 10I,46I,71T,77I,90M           | 57K,63P,93L              |
| 15 | 46I,84V,90M                   | 20I,63Q                  |
| 16 | 10I,46I,77I,84V,90M           | 63P,73T,93L              |
| 17 | 46I,77I,90M                   | 10F,20L,63P              |

TABLE 14-continued

Genotypic differences, which lead to improvement of predicting phenotypes

|    | Identified mutations          | Additional polymorphisms |
|----|-------------------------------|--------------------------|
| 18 | 36I,71T,90M                   | 63P,93L                  |
| 19 | 54V,71V,82A                   | 63P,93L                  |
| 20 | 77I,88S                       | 13V, 63P, 93L            |
| 21 | 10I,77I,84V,90M               | 63Q                      |
| 22 | 10I,20R,36I,71V,73S,84V,90M   | 13V,63P                  |
| 23 | 10I,46I,77I,90M               | 20I,63P,73T              |

TABLE 15

Predicted drug resistance level against the actual ones using 30 mutations

| Actual | S  | I  | R   |
|--------|----|----|-----|
| S      | 83 | 10 | 4   |
| I      | 3  | 22 | 4   |
| R      | 2  | 10 | 127 |

TABLE 17

Predicted drug resistance level against the actual ones using 90 mutations/polymorphisms

| Actual | S  | I  | R   |
|--------|----|----|-----|
| S      | 88 | 7  | 2   |
| I      | 5  | 21 | 3   |
| R      | 1  | 3  | 135 |

The improvement in prediction by adding new polymorphisms indicated that the NN model has an ability to identify new mutations. Statistical analysis demonstrated that the predicted phenotypes correlate to the actual phenotypes and the results in this example also demonstrated the accuracy of NNs in predicting the magnitude of resistance to protease inhibitors based on genotypic mutations. The performance of the neural network model is expected to improve given that the size of the training samples used was rather small and since an NN becomes more 'knowledgeable' as the number of training samples increases.

All references, patents, and patent application cited herein are incorporated by reference in their entirety.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A method for predicting phenotypic resistance of Human Deficiency Virus (HIV) to a therapeutic agent comprising:
   (a) providing a neural network;
   (b) training a neural network on a training data set, whereby the training data set is generated from an HIV genotype-phenotype database, wherein each member of the training data set corresponds to a genetic mutation that correlates to a phenotypic resistance of HIV, said training being performed by
      i) propagating a training data set in a feed-forward fashion,
      ii) calculating the associated error, iii) back propagating the error,
iv) adjusting the weights in the neural network,
v) minimizing the error function by repeating the steps i), ii), iii), iv),
vi) inputting a testing data set to ensure proper training, said testing data set comprising members that correspond to at least one genetic mutation, the presence of which correlates to a phenotypic resistance of HIV to at least one therapeutic agent, which testing data set is different from the training data set:

(c) providing a determined HIV genetic sequence from a patient by
  i) obtaining an HIV sample from the patient,
  ii) obtaining the genetic sequence from the HIV sample; and
(d) predicting the phenotypic resistance of HIV to the therapeutic agent by inputting the determined genetic sequence into the trained neural network which computes the predicted phenotypic resistance of HIV to a therapeutic agent, wherein the phenotypic resistance is expressed as the fold-change in the $IC_{50}$ or $IC_{90}$ values of one or more therapeutic agents.

2. The method of claim 1, wherein the neural network is a three-layer feed-forward neural network.

3. The method of claim 2, wherein the three-layer feed forward network comprises:

(a) a set of input nodes, wherein each member of the set of input nodes corresponds to a mutation in the genome of the pathogen;

(b) a plurality of hidden nodes; and (c) a set of output nodes, wherein each member of the set of output nodes corresponds to a therapeutic agent used to treat the pathogen.

* * * * *

UNITED STATES PATENT AND TRADEMARK OFFICE
CERTIFICATE OF CORRECTION

PATENT NO. : 7,058,616 B1
APPLICATION NO. : 09/589167
DATED : June 6, 2006
INVENTOR(S) : Brendan Larder et al.

It is certified that error appears in the above-identified patent and that said Letters Patent is hereby corrected as shown below:

Column 1,
Line 61, delete "JAM" and insert -- JAMA --.

Column 2,
Line 37, delete "provid" and insert -- provide --.

Column 4,
Line 47, delete "$W_{jk}$)," and insert -- $w_{jk}$), --.

Column 8,
Line 53, delete "5, 834,758," and insert -- 5,834,758, --.

Column 9,
Line 11, delete "of the whether" and insert -- of whether --.
Line 57, delete "www.viraresistance.com." and insert -- www.viralresistance.com.--.

Column 14,
Line 57, delete "$W_{jk}$)," and insert -- $w_{jk}$), --.

Column 20,
Line 2, delete "$X_2$," and insert -- $x_2$, --.
Line 10, delete "$y_{max}^i$ and minimum $y_{min}^i$" and insert -- $y^i_{max}$ and minimum $y^i_{min}$ --.
Line 21, delete "$y_{min}^i$" and insert -- $y^i_{min}$ --.
Line 22, delete "$y_{max}^i$" and insert -- $y^i_{max}$ --.
Line 49, delete "a was set" and insert -- α was set --.

Column 21,
Line 13, delete "h" and insert -- $h$ --.
Line 14, delete "h" and insert -- $h$ --.

UNITED STATES PATENT AND TRADEMARK OFFICE
CERTIFICATE OF CORRECTION

| | |
|---|---|
| PATENT NO. | : 7,058,616 B1 |
| APPLICATION NO. | : 09/589167 |
| DATED | : June 6, 2006 |
| INVENTOR(S) | : Brendan Larder et al. |

It is certified that error appears in the above-identified patent and that said Letters Patent is hereby corrected as shown below:

Column 30,
In Table 12, line 30, delete "R/P" and insert -- R/R --.

Signed and Sealed this

First Day of May, 2007

JON W. DUDAS
*Director of the United States Patent and Trademark Office*